(12) United States Patent
Abeliuk et al.

(10) Patent No.: US 11,574,703 B2
(45) Date of Patent: Feb. 7, 2023

(54) METHOD, APPARATUS, AND COMPUTER-READABLE MEDIUM FOR EFFICIENTLY OPTIMIZING A PHENOTYPE WITH A COMBINATION OF A GENERATIVE AND A PREDICTIVE MODEL

(71) Applicant: TeselaGen Biotechnology Inc., San Francisco, CA (US)

(72) Inventors: Eduardo Abeliuk, Oakland, CA (US); Andrés Igor Pérez Manríquez, Santiago (CL); Juan Andrés Ramírez Neilson, Santiago (CL); Diego Francisco Valenzuela Iturra, Santiago (CL)

(73) Assignee: TESELAGEN BIOTECHNOLOGY INC., San Francisco, CA (US)

( * ) Notice: Subject to any disclaimer, the term of this patent is extended or adjusted under 35 U.S.C. 154(b) by 89 days.

(21) Appl. No.: 17/240,553

(22) Filed: Apr. 26, 2021

(65) Prior Publication Data
US 2021/0257049 A1   Aug. 19, 2021

Related U.S. Application Data

(63) Continuation-in-part of application No. 16/725,642, filed on Dec. 23, 2019.
(Continued)

(51) Int. Cl.
*G06F 17/00* (2019.01)
*G16B 20/20* (2019.01)
(Continued)

(52) U.S. Cl.
CPC .......... *G16B 20/20* (2019.02); *G06N 3/0454* (2013.01); *G06N 3/08* (2013.01); *G16B 40/00* (2019.02)

(58) Field of Classification Search
CPC ........ G16B 20/20; G16B 20/00; G16B 40/00; G16B 40/20; G06N 3/0454; G06N 3/08; G06N 3/0472; G06N 3/0445; G06N 5/04
See application file for complete search history.

(56) References Cited

U.S. PATENT DOCUMENTS

| | | | |
|---|---|---|---|
| 8,868,472 B1 * | 10/2014 | Lin ..................... | G06N 5/02 706/12 |
| 10,929,756 B1 * | 2/2021 | Sadaghiani ............ | G06N 5/045 |
| 2020/0320125 A1 * | 10/2020 | Albonetti ............ | G06F 11/3452 |

OTHER PUBLICATIONS

Dan He et al., SAME: a sampling-based multi-locus epistasis algorithm for quantitative genetic trait prediction. Proceedings of the 6th ACM Conference on Bioinformatics, Computational Biology & Health Informatics, Asso. for Computing Machinery, 286-295, <https://doi.org/10.1145/2808719.280>, Sep. 2015.*

* cited by examiner

*Primary Examiner* — Greta L Robinson
(74) *Attorney, Agent, or Firm* — Amardeep S. Grewal; Reed Smith LLP

(57) ABSTRACT

A method, apparatus, and computer-readable medium for efficiently optimizing a phenotype with a combination of a generative and a predictive model, training a phenotype prediction model based on experiential genotype vectors, training a genotype generation model based on sample genotype vectors, generating new genotype vectors, applying the phenotype prediction model to the new genotype vectors to generate scores, determining result genotypes based on a ranking of the available genotypes according to the scores, and generating a result based on the result genotypes, the result indicating one or more genetic constructs for testing.

36 Claims, 18 Drawing Sheets

Related U.S. Application Data

(60) Provisional application No. 63/015,140, filed on Apr. 24, 2020.

(51) Int. Cl.
*G06N 3/04* (2023.01)
*G06N 3/08* (2023.01)
*G16B 40/00* (2019.01)

METHOD, APPARATUS, AND COMPUTER-READABLE MEDIUM FOR EFFICIENTLY OPTIMIZING A PHENOTYPE WITH A COMBINATION OF A GENERATIVE AND A PREDICTIVE MODEL

RELATED APPLICATION DATA

This application claims priority to U.S. Provisional Application No. 63/015,140, filed Apr. 24, 2020, and titled "PREDICTIVE AND A GENERATIVE MODEL TO OPTIMIZE THE HIGHLY DIMENSIONAL EXPLORATION OF OPTIMUM SOLUTIONS," the disclosure of which is hereby incorporated by reference in its entirety. This application is also a continuation-in-part of U.S. Nonprovisional application Ser. No. 16/725,642, filed Dec. 23, 2019, and titled "METHOD, APPARATUS, AND COMPUTER-READABLE MEDIUM FOR EFFICIENTLY OPTIMIZING A PHENOTYPE WITH A SPECIALIZED PREDICTION MODEL," the disclosure of which is hereby incorporated by reference in its entirety.

BACKGROUND

A recurrent problem in synthetic biology is to find the genetic sequence that optimizes, for a given biological system, the production of a specific molecule or compound, or more generally that optimizes a specific metric that characterizes the phenotype of a given biological system. In general this search can be quite expensive because it requires numerous experiments. Evaluating the performance and characterizing the phenotype of different genetic variants can consume a lot of time and resources.

Instead of searching for an optimal genetic design within the universe of all possible genetic sequences, it becomes important to focus the search to certain known variants of genes or parts of DNA directly involved in the production of the compound, or phenotype of the corresponding biological system. Despite the narrowing of the search space to be explored, the number of possible genetic designs is typically quite large and it is necessary to have tools that allow finding the optimal genetic design with the smallest number of experiments as possible.

Unfortunately, even with a reduced search space, it is completely unfeasible for a geneticist to implement and collect results from even a small fraction of the possible genetic designs, as the number of combinatorial possibilities scales exponentially according to the number of component genotype variants.

Additionally, attempts to reduce the search space using automated techniques and algorithms are also impractical due to both the exponential computational complexity of the search problem and the difficulty in quantifying the phenotype expressions for genotype sequences which have not previously been assessed experimentally.

Even predictive models that utilize an acquisition function to evaluate the search/solution space can sometimes be insufficient to identify an optimal sequence. For example, in situations where the dimensionality of the solution space is very large, evaluating an acquisition function on all its points makes is virtually impossible. Another problem is that in input spaces with high dimensionality, the distribution of experimental data points has a small compact support. This makes it difficult (probabilistically) to sample new data points that are valid candidates.

Accordingly, improvements are needed in technology for predictive modeling of the phenotype of a biological system and efficiently optimizing a phenotype.

DETAILED DESCRIPTION

Figure 1:
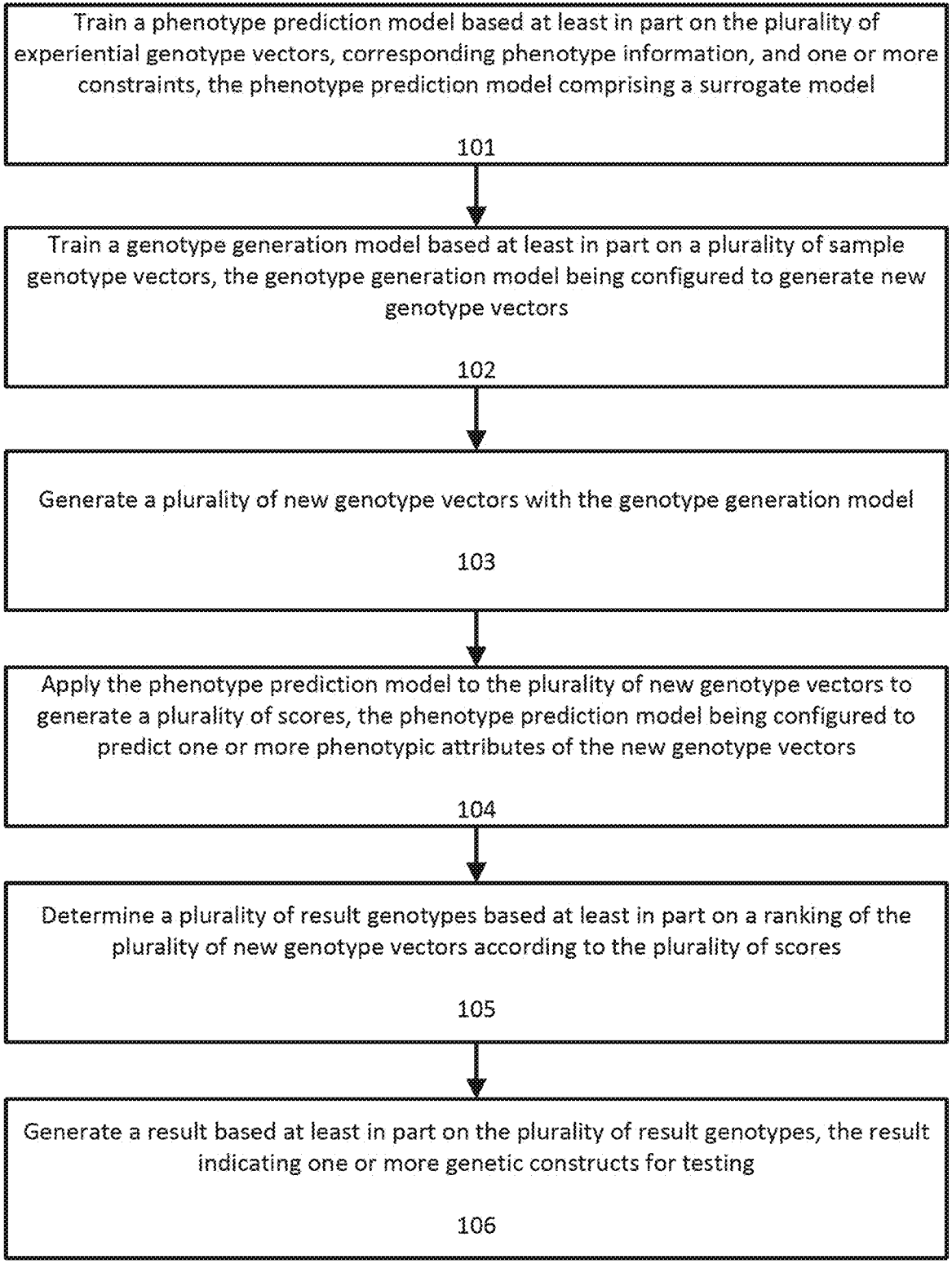
FIG. 1 illustrates a flowchart for efficiently optimizing a phenotype with a combination of a generative and a predictive model according to an exemplary embodiment.

While methods, apparatuses, and computer-readable media are described herein by way of examples and embodiments, those skilled in the art recognize that methods, apparatuses, and computer-readable media for efficiently optimizing a phenotype with a combination of a generative and a predictive model are not limited to the embodiments or drawings described. It should be understood that the drawings and description are not intended to be limited to the particular form disclosed. Rather, the intention is to cover all modifications, equivalents and alternatives falling within the spirit and scope of the appended claims. Any headings used herein are for organizational purposes only and are not meant to limit the scope of the description or the claims. As used herein, the word "can" is used in a permissive sense (i.e., meaning having the potential to) rather than the mandatory sense (i.e., meaning must). Similarly, the words "include," "including," and "includes" mean including, but not limited to.

As discussed above, while running new experiments to optimize the phenotype of the biological system (such as the titer of a metabolite), it would be useful to have a system that optimizes the phenotype of a biological system based on experimental data previously obtained and that also reduces the computational complexity of the search problem so that a possible solution set can be determined in a feasible time. Researchers would then have additional information that would allow them to make better decisions regarding which experiments to perform.

Additionally, improved methods and systems are needed for optimization problems where the dimensionality of the solution space is very large, and where evaluating an acquisition function on all its points is impossible.

Applicant has discovered a method, apparatus, and computer-readable medium for efficiently optimizing a phenotype with a combination of a generative and a predictive model. The prediction model is constructed specifically to optimize the phenotype of a biological system by generating phenotype predictions relating to genotypes which have not been experimentally characterized and which meet a user's requirements. The disclosed method, apparatus, and computer-readable medium are further configured to reduce the computational complexity of exploring the search space of possible genotypes using a variety of specialized heuristics adapted to this domain and, in some cases, adapted to the hardware that is used to apply the prediction model.

The novel method, apparatus, and computer-readable medium disclosed herein generates and progressively adjusts a generative model together with a predictive model. These models are configured to generate new optimized data in the sense of a specific metric associated with a particular quality of interest. This algorithm is based on a generative model capable of generating "new" valid (real-looking) data configured to optimize a particular quality or property, and there is also a predictive model capable of predicting the value of such property for this new data which of course has not yet been experimentally characterized.

The described process for generating and adjusting a generative and a predictive model is described in the context of optimizing the phenotype of a biological system. These models are used in tandem to optimize the exploration of untested genotypes. However, the described method of utilizing Sequential Model Based Optimization (SMBO) with a predictive model with uncertainty estimation as a surrogate together with a generative model as a candidate provider is applicable to any task involving optimization of the input of a black-box function (i.e., control parameters of a dynamic system).

The disclosed method, apparatus, and computer-readable medium serves as a solution for optimization problems where the dimensionality of the solution space is very large, and where evaluating an acquisition function on all its points is not possible. Also, in input spaces with high dimensionality, the distribution of experimental data points has a small compact support. This makes it difficult (probabilistically) to sample new data points that are valid candidates. In the proposed approach the generative model is used to sample valid data points by correctly exploring the multidimensional space around the support of the experimental data. Also, the predictive model is used by the generator in order to improve its sampling towards the generation of more efficient candidates that can better explore the solution space.

FIG. 1 illustrates a flowchart for efficiently optimizing a phenotype with a combination of a generative and a predictive model according to an exemplary embodiment. As shown in FIG. 1, the disclosed process utilizes experiential genotype vectors and to train a phenotype prediction model (also referred to herein as the "predictive model," the "prediction model," or the "predictor model") and sample genotype vectors to train a genotype generation model (also referred to as the "generative model," the "generation model," or the "generator model").

The experiential genotype vectors are determined based upon experimental data and the sample genotype vectors are determined based upon a sample database. In some cases the experiential genotype vectors can reflect the underlying structure of the genotype information in the experimental data and the sample genotype vectors can reflect the underlying structure of the genotype information in the sample data. However, in situations where the genotype information in the experimental database is stored in a different format or includes different attributes, the underlying dataset can be transformed/encoded to generate the experiential genotype vectors. Similarly, if the genotype information in the sample database is stored in a different format or includes different attributes, the underlying dataset can be transformed/encoded to generate the sample genotype vectors.

Figure 2:
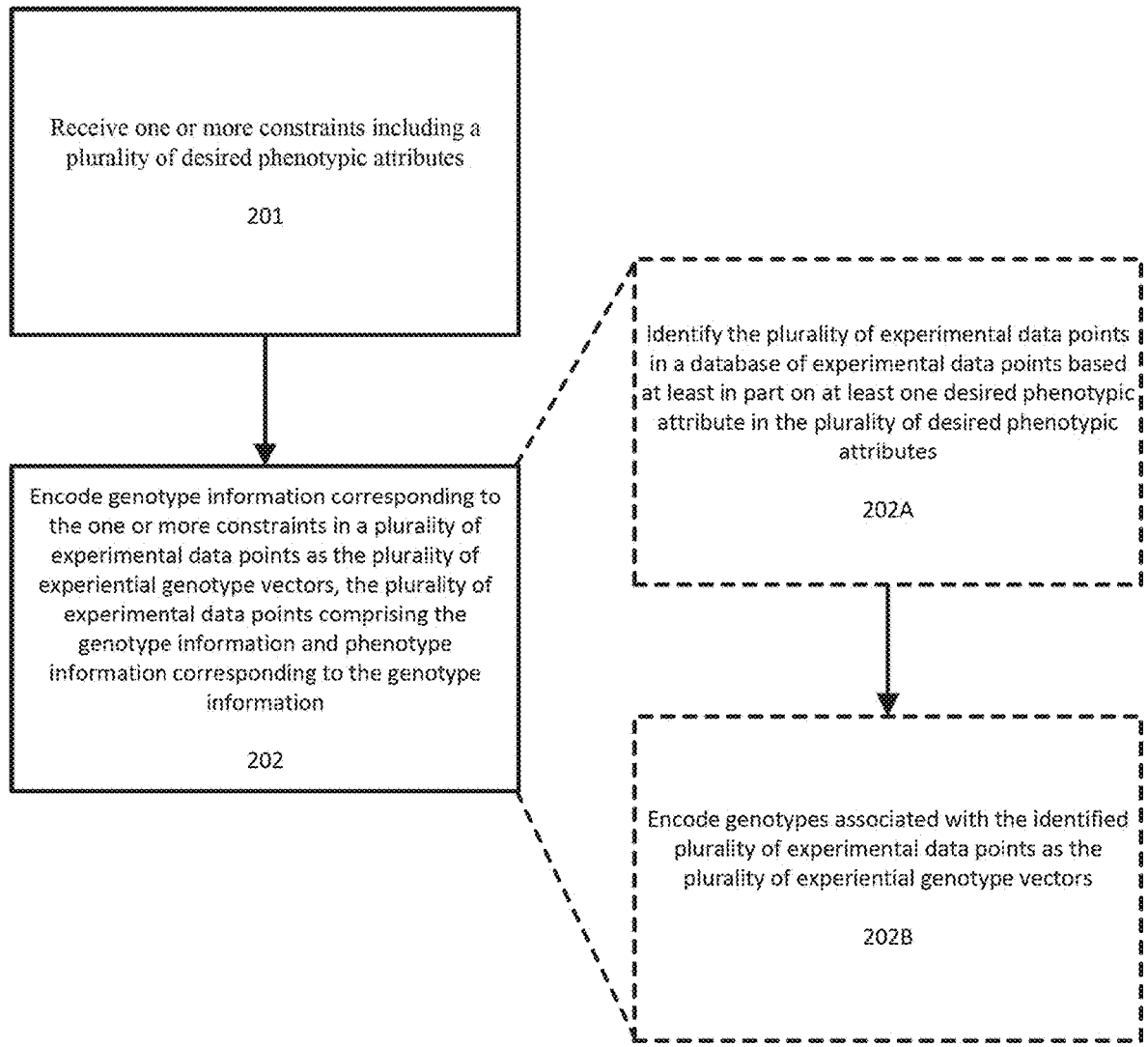
FIG. 2 illustrates a flowchart for encoding genotype information in a plurality of experimental data points corresponding to a set of constraints as a plurality of experiential genotype vectors according to an exemplary embodiment.

The experiential genotype vectors can be generated from genotype information in an experimental database based at least in part on one or more constraints. FIG. 2 illustrates a flowchart for encoding genotype information in a plurality of experimental data points corresponding to a set of constraints as a plurality of experiential genotype vectors according to an exemplary embodiment.

At step 201 one or more constraints are received. The one or more constraints are constrains particular to a specific user's goals, experimental conditions, limitations, or other factors relating to the desired output from the predictive model. The one or more constraints can include a plurality of desired phenotypic attributes. The plurality of desired phenotypic attributes correspond to the phenotypes that a user is seeking to optimize through use of the system and subsequent experimentation.

Optionally, the one or more constrains can also include a plurality of available genotypes. The plurality of available genotypes can correspond to the genotypes that a particular user is able to create or has access to for experimental purposes. As the novel method and system disclosed herein limits the search space for the optimization problem through the use of a generative model, it is not necessary for the constraints to include plurality of available genotypes. The limitations on available genotypes can also be input into the system through the choice of training data for the generative model, as discussed in greater detail below.

One of skill in the art will of course understand that genotype refers to a genetic constitution or sequence and phenotype refers to an observable characteristic resulting from the interaction of a genotype with a particular environment. A phenotype can include, for example, the ability of a particular genotype to produce a specified molecule, compound or metabolite (determined by the titer of the molecule), bacterial growth (determined by optical density data), resistance of a strain to extreme conditions and temperature, salinity, or pH conditions, etc.

The constraints can be received from a user via an input interface or in a communication via a network interface. The constraints can also be received from a software process or computing system via a messaging protocol, a network connection, or other communication mechanism.

The step of receiving the constraints can include the user specifying the pool of variants that should be explored for each bin. The user can use just the labels or, alternatively, the genetic/amino-acid sequences if using a sophisticated embedding approach. The user also needs to specify the property to be optimized (this means that the user has to provide, for example, the name of the column that contains the target value in the database). The algorithm will always try to maximize that phenotypic value, so the user should be aware of that and perform a transformation on the property if required to obtain a benefit from the process. A common transformation is, for example, multiplying all values by −1 in order to minimize the original phenotype measurement.

At step 202 genotype information in a plurality of experimental data points corresponding to the set of constraints is encoded as a plurality of experiential genotype vectors, the plurality of experimental data points comprising the genotype information and phenotype information corresponding to the genotype information.

This step can include, for example, interfacing and communicating with experimental database storing all experimental data points and extracting the plurality of experimental data points that correspond to the set of constraints. The experimental database can be a distributed database, such as a cloud database, that is accessible to a plurality of researchers. Each researcher can then upload experimental results to the database in order to provide additional training data for training the model, as will be discussed further below.

Each experimental data point can include phenotypic measurements and corresponding genotype data. For example, the experimental data point can include corresponding to a particular genetic sequence, gene, and/or gene fragment and can also include phenotypic measurements that correspond to that particular genetic sequence, gene, and/or gene fragment. The phenotypic measurements can be measurements that were experimentally determined in previous experiments. The experimental data points can be configured to link genotype data with phenotypic measurements in a memory of the database, such as through a relational database, directed graph, or other techniques.

Optionally, this step can include encoding all genotype information in the plurality of experimental data points as a plurality of experiential genotype vectors, irrespective of the constraints. For example, when the experimental dataset is small (say a few hundred constructs), all of these constructs can be used to generate the plurality of experiential genotype vectors.

It only contains the experiments that the scientists have already performed in the lab. This group of samples is a subset of all the possible candidates that you can build if you recombine the alleles (variants) that are present on those constructs. Thus, the group of all possible candidates is bigger, and can contain thousands or hundreds of thousands candidates As shown in FIG. 2, the step of encoding genotype information in a plurality of experimental data points corresponding to the set of constraints as a plurality of experiential genotype vectors (step 202) can include sub-steps 202A and 202B.

At step 202A the plurality of experimental data points are identified in a database of experimental data points based at least in part on one or more of: at least one available genotype in the plurality of available genotypes and at least one desired phenotypic attribute in the plurality of desired phenotypic attributes. This step can conduct a search of the database for all experimental data points that have genotypes matching or interchangeable with at least one genotype listed in the plurality of available genotypes. This step can also conduct a search of the database for all experimental data points that have phenotypic measurements matching at least one desired phenotypic attributes in the plurality of desired phenotypic attributes. As discussed earlier, phenotypic attributes can include, for example, the ability of a genotype to produce a specified molecule or compound.

At step 202B the genotypes associated with the identified plurality of experimental data points are encoded as a plurality of experiential genotype vectors. This encoding process is discussed in greater detail below. Of course, the genotypes associated with the identified plurality of experimental data points can be encoded in other ways, such as by representing the genotypes using a categorical or nominal representation correspond to categories/sequences/sub-sequences, etc. As part of the encoding process, the phenotypic measurements in the identified plurality of experimental data points can optionally also be encoded using one or more of the above-described schemes to later enable more efficient analysis.

A similar process to step 202B can be performed for generating the sample genotype vectors. In particular, genotype information in a plurality of sample genotypes of a sample database can be encoded as the plurality of sample genotype vectors. The encoding process can be the same encoding process used to generate the experiential genotype vectors and is discussed in greater detail below.

Note that while the sample genotypes can optionally be labeled and include phenotypic and other attributes, this is not required for training the generative model. All that is required for the sample genotypes is that they include genotype information (i.e., unlabeled data).

The plurality of sample genotypes can be selected in any way from the sample database, such as through random sampling. A user can optionally provide sample constraints relating to the sample genotypes to be selected. These constraints can be used to filter the sample genotypes selected from the sample database.

The user can exercise control over the results produced by the generative model through selection of the sample database itself. Since the training data for the generative model is sourced from the sample database, the selection of the sample database (and the selection of samples within that sample database) can be used to control the type of genotypes produced by the system. For example, when designing a protein (a sequence of amino acids) a user can select a sample database that includes only feasible proteins to minimize the likelihood that the generative model will produce sequences of amino acid letters that are not feasible proteins. The sample database can also be the same database used to generate the experiential genotype vectors (i.e., the experimental data).

Figure 3:
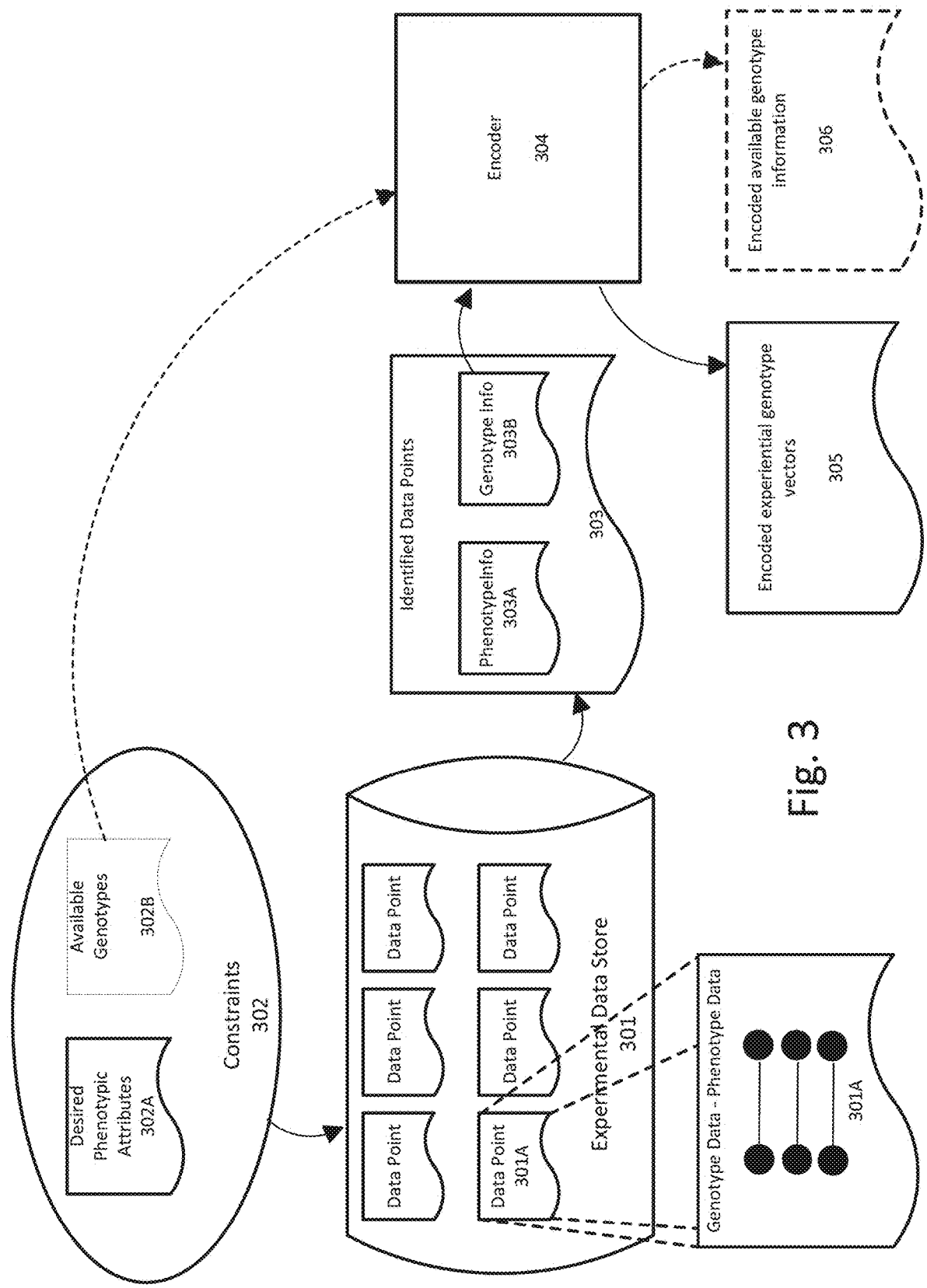
FIG. 3 illustrates a data flow chart showing the process for generating encoded experiential genotype vectors according to an exemplary embodiment.

FIG. 3 illustrates a data flow chart showing the process for generating encoded experiential genotype vectors according to an exemplary embodiment. As shown in FIG. 3, constraints 302 including a plurality of desired phenotypic attributes 302A and, optionally, a plurality of available genotypes 302B can be received. This receiving step can optionally include encoding the plurality of available genotypes 302B with an encoder 304 to generate encoded available genotype information 306. This data flow is shown by the dashed arrows. When using certain encoding schemes, such as embedding schemes (discussed below), the encoded available genotype information 306 can include a plurality of available genotype vectors.

As additionally shown in FIG. 3, the constraints 302 are applied to the experimental data store 301, containing multiple experimental data points, to identify a plurality of experimental data points 303 corresponding to the constraints 302. Data point 301A illustrates an example of how genotype data can be linked to corresponding phenotype data within each experimental data point. The identified experimental data points 303 will include genotype information 303B and phenotype information 303A corresponding to the genotype information 303B. The genotype information 303B is then supplied to the encoder 304, which encodes it to generate encoded experiential genotype vectors 305. The different encoding techniques that can be used by the 304 encoder are discussed in greater detail below.

Figure 4:
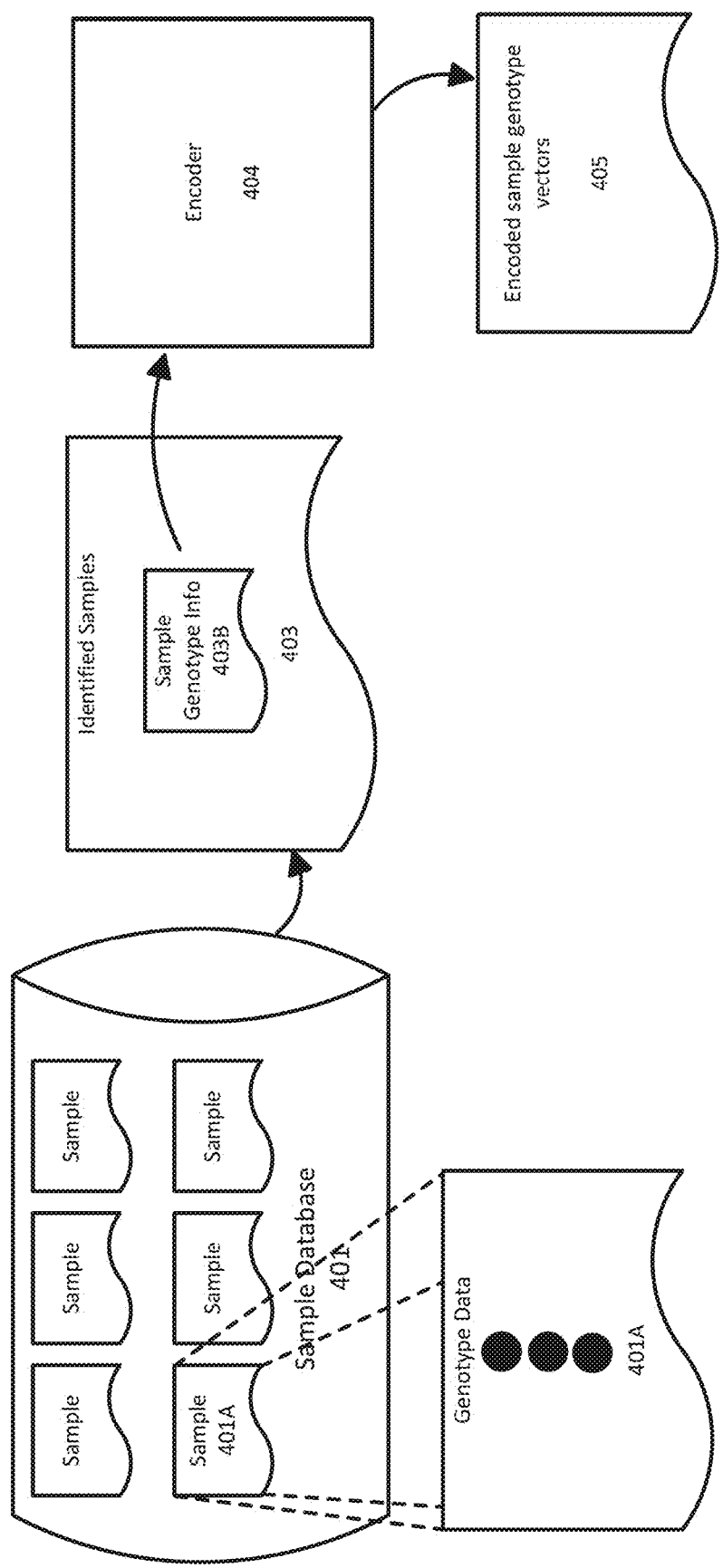
FIG. 4 illustrates a data flow chart showing the process for generating encoded sample genotype vectors according to an exemplary embodiment.

FIG. 4 illustrates a data flow chart showing the process for generating encoded sample genotype vectors according to an exemplary embodiment. As shown in FIG. 4, a sample database 401 includes multiple samples, such as sample 401A, including genotype data. All that is required is that each of the samples include genotype data, but of course the samples can optionally include additional data, such as phenotype information. A plurality of identified samples 403 are selected and extracted from the sample database 401. As discussed earlier, these samples can be selected in any way, such as through random sampling, a user-defined process, or filtering based upon one or more sample constraints. The identified samples 403, including sample genotype information 403B, are provided to the encoder 404. The samples 403 are encoded by the encoder 404 to generate encoded sample genotype vectors 405.

Encoding DNA Parts Using Embeddings for Sequential Model Based Optimization (SBMO) Strategy As will be discussed in greater detail further below, the disclosed systems and method can be implemented using SBMO. The SBMO strategy for biological systems can be applied using different ways to represent data. The most direct way is to just use labels. With the "label representation" the gene variants and promoter sequences are represented with nominal variables, so the model is expected to learn from data how these labels are related to each other and how they affect the outcome. This kind of representation is very easy to implement and test and it doesn't need the use of the variant's genetic sequences. It just needs labels to be able to distinguish between nominal categories among the features. The drawback is that, as it can't use sequence information, the model could miss the underlying biochemical information that can be useful for the prediction task.

In order to be able to use information from DNA/Protein sequences, alternative ways to represent data can be utilized. These methods utilize Natural Language Processing and are focused on building low-dimensional numerical representations (embeddings) of text sequences. The use of a continuous numerical representation provides biological and chemical information about the variants that the learner (surrogate model) could use to make better predictions, improving the efficiency in getting an optimal design.

The building of the embeddings requires the training of machine learning models on vasts amounts of data. The number of sequences involved in the problems SBMO should apply are typically low, so the model that encodes the text information needs to be trained previously on external large datasets. This transfer learning methodology allows a model to apply knowledge from a large dataset to a more specific task.

Encoding Via Multidimensional Representation of Sequences

Through embedding techniques, sequences can be represented as vectors that lie in a multidimensional space. These vectors encode sequence information and allows making relationships in the multidimensional space that have biochemical and biophysical sense. This dense representation in a continuous space makes it possible for the model to have access to information about the sequences that allows the model to identify, extract and exploit the relationships between them.

To model biological sequences natural language processing techniques can be utilized. For this, we consider a sequence as a composition of sub units represented by symbols or sequences of symbols, which we call tokens. Each sequence is related to a set of tokens. In our case, these tokens can be defined as n-grams, where a n-gram is a sequence of n contiguous sequence elements. The parameter n can take values between 1 and the maximum length of all the sequences, where the length is measured according to the maximum amount of the smallest subunits in which it is possible to divide the sequence. For example in the case of proteins, these n-grams correspond to their (sub)sequences of n residues, and in the case of genes, correspond to their (sub)sequences of n nucleotides or codons, etc.

A parametric model, such as a neural network with one or more layers, can be utilized to learn a multidimensional representation for each token. This can be done using a representation learning algorithm (such as Word2Vec, GloVe, FastText, Autoencoders, Variational Autoencoders (VAEs), ProtVec and GeoVec, dna2vec, etc.)

The above method allows for representation of larger sequences using, for example, a weighted sum of n-grams. This weighting can be learned by a parametric model such as a neural network with one or more layers. It can also be the arithmetic sum, the average, the weighting by the inverse of the frequency of the tokens, among others. The resulting representation contains enough information, for example, to group the sequences according to their biochemical and biophysical properties.

Similar methods can be used to train Language Models that directly translate sequences into vector representations, without defining explicitly an arithmetic for combining token representations. Some of these approaches include the training of Recurrent Neural Networks on token prediction tasks or use models like Autoencoders, VAEs, BERT, etc.

When using the embedding approach, the input of the surrogate will be fully continuous. Hence, the SBMO might take advantage of this and use a surrogate model with analytical optimum (such as Gaussian Process) or derivable (such as Deep Ensembles, Deep Gaussian Processes, Bayesian Networks or other Bayesian approaches). In case of using a derivable model, optimum can be searched by means of Gradient Descent algorithm, Stochastic Gradient Descent or similar.

The above-described encoding/embedding and corresponding decoding schemes can be utilized for encoding/decoding the experiential genotype vectors (such as by encoder 304 in FIG. 3) and the sample genotype vectors (such as by encoder 404 in FIG. 4).

Returning to FIG. 1, at step 101 a phenotype prediction model is trained based at least in part on the plurality of experiential genotype vectors, the corresponding phenotype information, and the one or more constraints.

The phenotype prediction model is a surrogate model (sometimes referred to as a metamodel or a substitute model) that is used to approximate an objective function. A surrogate model (also referred to as a "surrogate function") is a model that approximates the behavior of a more complex model or physical system as closely as possible. Surrogate models are explained in greater detail below and can be utilized when the computational complexity of a physical system, experimental data points, and/or constraints would result in computationally indeterminable or infeasible training or application steps.

Surrogate Model

In some real-world optimization problems, it is not always possible to directly obtain analytical solutions. These kinds of objective functions are called "black-box" functions and describe a situation where there is no expression of the objective function that can be analyzed, and it's not possible to know its derivatives. Evaluating the function is restricted to querying at a point x and getting a (possibly noisy) response. Due to the above-mentioned challenges, the optimization formulation can be updated by replacing the objective function $f(\bullet)$ with a surrogate objective function $\tilde{f}(\bullet)$ such that they share the same optimal solutions. Thus solving the optimization for $\tilde{f}(\bullet)$ must also solve the optimization for $f(\bullet)$ as expressed below.

$$\operatorname*{argmin}_{x_s \in X_b} \tilde{f}(x_s) \simeq \operatorname*{argmin}_{x_b \in X_B} f(x_s)$$

Finding a suitable $\tilde{f}(\bullet)$ may also be a non-trivial task. One approach is to represent it as a parametric model with parameters $\theta_f$ such $\tilde{f}_{\theta_f}(\bullet) \equiv \tilde{f}(\bullet)$. Attaining the optimal parameters is in itself another optimization problem that may be expressed as follows.

$$\theta_j^* = \operatorname*{argmin}_{\theta_f \in \Theta_f} M\left[\tilde{f}_{\theta_f}(\cdot), f(\cdot)\right]; x_{s_i} \in X_s \subseteq X \qquad 1.2$$

Where M is some measure of distance between its arguments. In other words, we are looking for parameters $\theta^*_f$ such that the distance M between $\tilde{f}(\bullet)$ and $f(\bullet)$ is minimized, for a subset $\{x_{s_i}\}_{i=1}^N$ of N elements from the solution space (in practice this subset corresponds to the available experimental data). These elements are used to optimize the parametric function $\tilde{f}_{\theta_f}$, so that it is informative enough to perform a successful optimization.

Sequential Model Based Optimization is used to train the surrogate model and is explained in greater detail below.

Sequential Model Based Optimization (SMBO)

SMBO algorithms are a family of optimization methods based on the use of a predictive model to iteratively search for the optimum of an unknown function. They were originally designed for experimental design and oil exploration. SMBO methods are generally applicable to scenarios in which a user wishes to minimize some scalar-valued function $f(x)$ that is costly to evaluate. These methods progressively use the data that is compiled from a process or objective function to adjust a model (i.e., the surrogate model). This model is used on each iteration to make predictions of the objective function over a set of candidates, which are ranked according to their predicted score. On each iteration, the top ranked candidate is suggested to be evaluated for the next iteration.

SMBO has never been applied before to the optimization of a biological system, which poses specific challenges that are addressed by the methods, apparatuses, and computer-readable media disclosed herein.

When ranking candidates, SMBO methods usually use a scalar score that combines the predicted value with an estimation of its uncertainty for each sample. The intuition behind using the uncertainty is that the reliability of the predictions may decrease on unexplored areas of the solution space. Also, the consideration of an uncertainty term in the acquisition function promotes the exploration and the diversity of recommendations, helping to avoid local optima. There are many options for acquisition functions in literature. One of the most commonly used is the expected improvement (EI).

There can be found several SMBO methods in literature. These methods differ from the present system on the modeling approach. One of the most known methods is called Bayesian Optimization, which uses Gaussian Processes (GP) as a surrogate model. This approach has been successfully applied in many fields, however GP modeling cannot be applied directly to discrete variables (like genotypes). Other approaches include Hyperopt (or TPE algorithm) which uses a Tree-Structured Parzen Estimator and SMAC which uses Random Forests (RF) as surrogate model.

As noted before, one of the most common acquisition functions is called Expected Improvement (EI). The general formulation is:

$$EI(x)=E[f(x)-f(x^*)]$$

where $f(x^*)$ is the current optimum value and $f(x)$ is the value of the surrogate's prediction. As it is required a random variable to calculate expectancy, $f(x)$ should be associated with a probability function. Unfortunately, with most machine learning models it's not trivial to obtain a distribution of a prediction (instead of just a plain prediction value) to be used as surrogate. For this, a possible approach (among a few others) is to use Ensemble models (e.g., Random Forests, Deep Neural Network Ensembles, implicit ensembles, or Bayesian models, Deep Gaussian Processes, etc.). With Random Forests (RF), the RF prediction is used as an estimation of the statistical mean of the surrogate model's predictions, for which a gaussian distribution is assumed. The calculation of the variance of the prediction considers RF's estimators deviation and the leaf training variance for each tree. Both estimations are combined using the Law of total variance.

Classic SMBO approaches are formulated to recommend one experimental observation per iteration. However, in the context of optimizing a biological system, a single experiment can typically make multiple evaluations of the objective function. In those cases, experimental recommendations should be grouped into batches, and the method should be able to suggest on each iteration a batch of n candidates $x_j$ when $j \in \{1, \ldots, n\}$ instead of just one single recommendation.

The simplest way to recommend a batch of n experiments is to get the n optimal values from the acquisition function. However, this criterion ("take the n designs with highest acquisition values") may not consider that some designs in the selected set may be very close to each other, reducing solution's space exploration and incurring in wasteful experimental evaluations. A possible strategy to deal with batch suggestions is the use of the constant liar technique. With this technique, the first candidate, $x_1$, is obtained by maximizing the acquisition function in the same way as for the single sample case. However, to obtain $x_{j+1}$ it is assumed that the evaluation at point $x_j$ exists, and the model is retrained adding a fabricated value for $x_j$'s evaluation into the training dataset. Then, the new acquisition function is maximized to obtain the next candidate. There are several heuristics that could be used to decide how to fabricate $x_j$'s evaluation value (ex: use the mean predicted value $\mu$ or; the mean prediction plus the deviation $\mu+\sigma$ or; the prediction mean minus sigma $\mu-\sigma$, etc).

Figure 5:
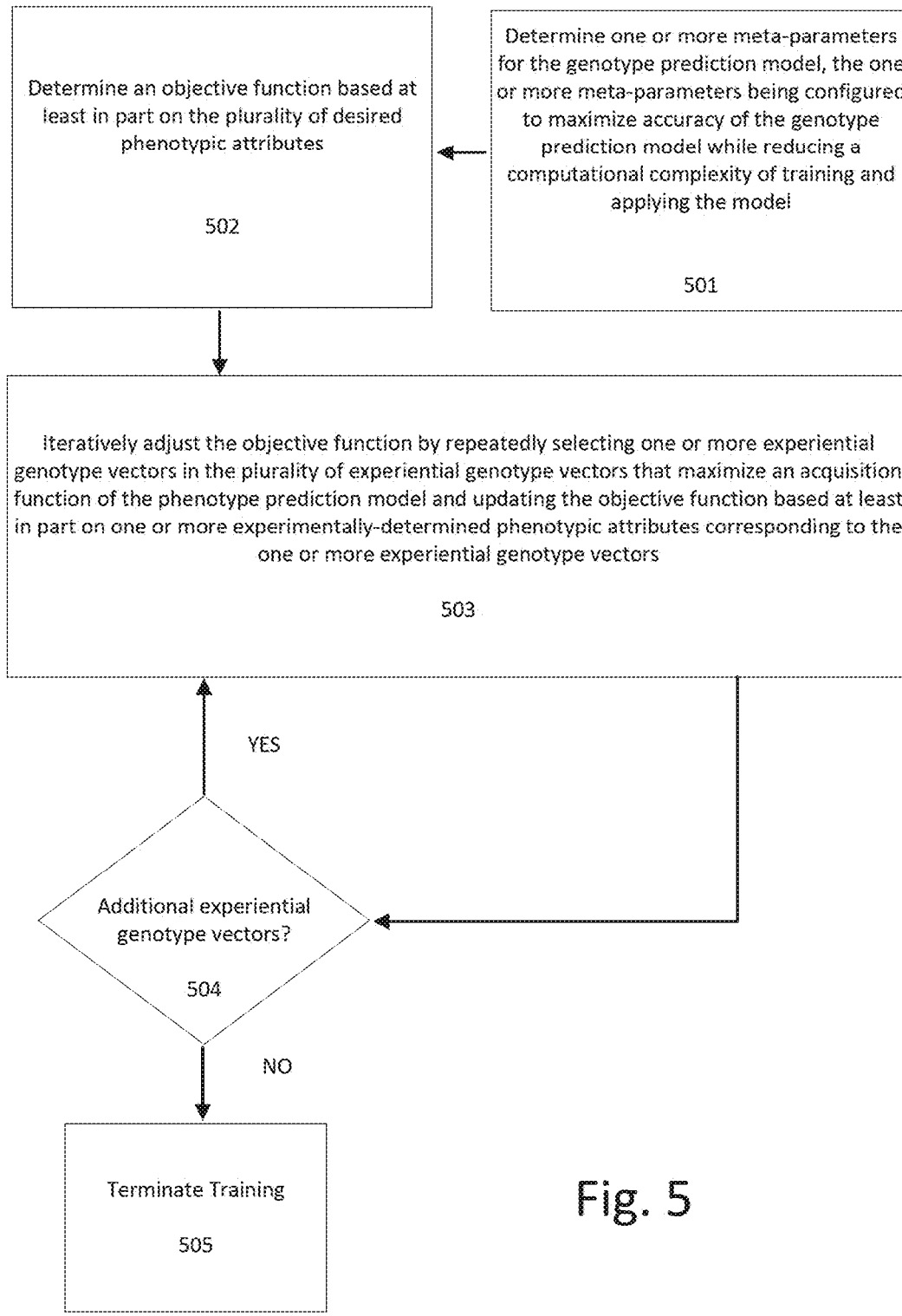
FIG. 5 illustrates a flowchart for training a phenotype prediction model based at least in part on the plurality of experiential genotype vectors, the corresponding phenotype information, and the one or more constraints according to an exemplary embodiment.

FIG. 5 illustrates a flowchart for training a phenotype prediction model based at least in part on the plurality of experiential genotype vectors, the corresponding phenotype information, and the one or more constraints according to an exemplary embodiment.

At step 501 one or more parameters are determined for the surrogate model, the one or more parameters being configured to maximize accuracy of the surrogate model while reducing a computational complexity of training and applying the model.

Figure 6:
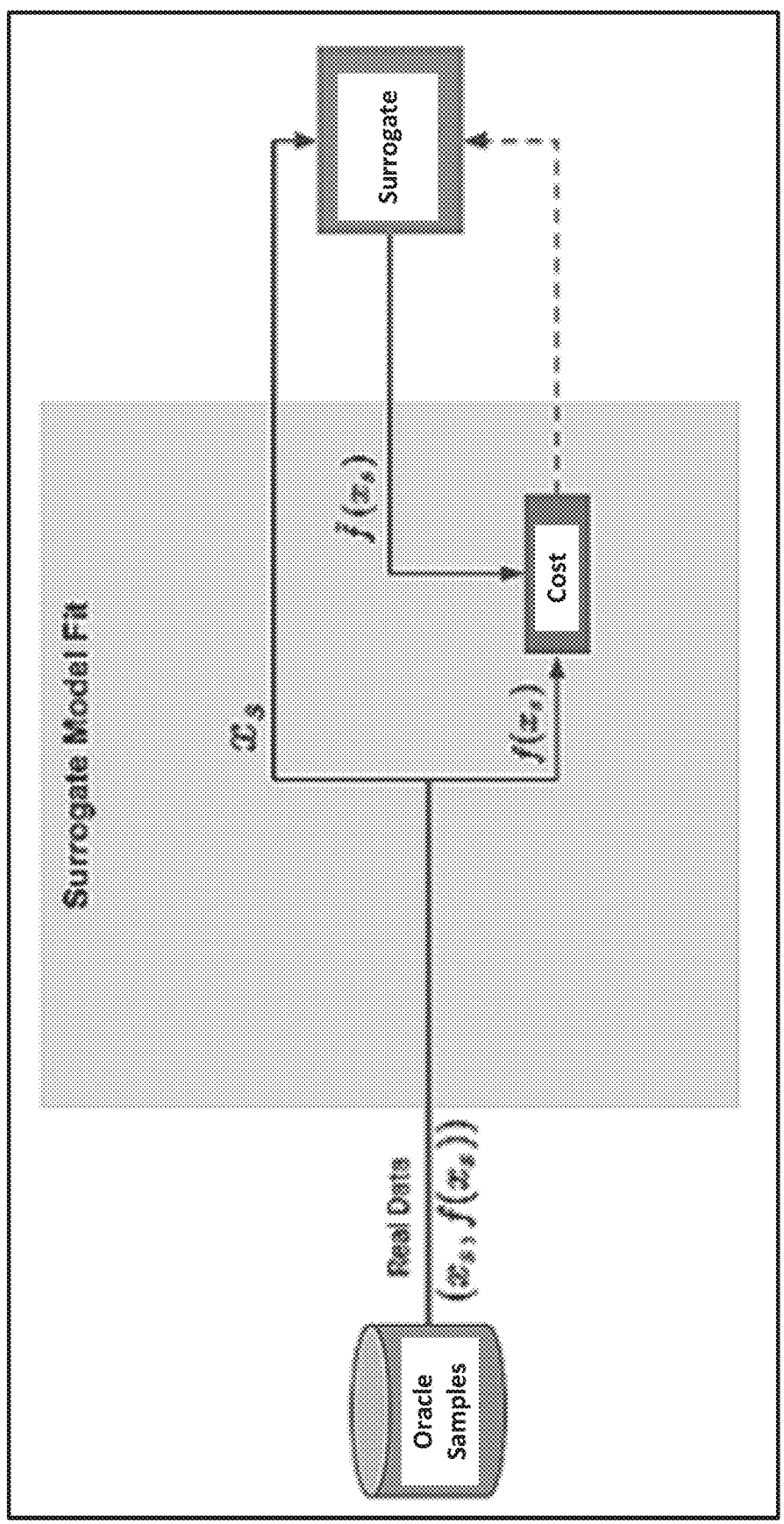
FIG. 6 illustrates a diagram of the parameter adjustment algorithm of the surrogate model according to an exemplary embodiment.

FIG. 6 illustrates a diagram of the parameter adjustment algorithm of the surrogate model according to an exemplary embodiment. The surrogate is a model that not only makes predictions, but also quantifies the uncertainty of its estimations on data that haven't been yet observed (hasn't been evaluated by the oracle, described in greater detail below). To adjust its parameters, it is required to observe a threshold amount of data that will depend on the nature of the problem as well as the architecture of the model.

Within the current implementation, it is considered a surrogate model based on Deep Ensembles (an ensemble of deep neural networks). This model is readily parallelizable, requires very little hyperparameter tuning, and yields high quality predictive uncertainty estimates.

The training scheme for the surrogate model is described in FIG. 6. Here, $\hat{f}(\bullet)$ is evaluated in $x_s$, and its output $\hat{f}(x_s)$ is compared with the target value $f(x_s)$ that has been labeled by the oracle. Then, the distance between them is computed, what we call cost. The Surrogate Model parameters $\theta_f$ are adjusted so that the value of this cost function is minimized. The parameters are adjusted using an optimizer with default parameters.

FIG. 6 shows a diagram of the parameter adjustment algorithm of the surrogate model $\hat{f}(\bullet)$. Data points labeled by the oracle are used (Oracle samples). The Oracle samples refer real-world results, such as the experimental data points previously discussed (linking genotype data to phenotype data). Optionally, the Oracle samples can be derived in ways other than experimentation. For example, in certain scenarios, it may be possible to mathematically derive results by modeling the molecular/biological behavior. These mathematically derived results can also correspond to real-world behavior.

The tuple $(x_s; f(x_s))$ represents a labeled data point (where $x_s$ refers to a sample point and $f(x_s)$ refers to its evaluation in the oracle), and $\hat{f}(x_s)$ corresponds to the surrogate model evaluation of the given sample. The update of the parameters of the surrogate model is done in a way to reduce the cost function that receives $f(x_s)$ and $\hat{f}(x_s)$ as arguments, this update is indicated by the dotted arrow.

Once the parameters that define the architecture of the model have been found, the SMBO logic can be applied to determine the next points to evaluate experimentally and to successively update the predictive model until the most optimal phenotype has been determined.

Returning to FIG. 5, at step 502 an objective function is determined based at least in part on the plurality of desired phenotypic attributes. The process of recommending genotypes for experimentation involves maximization of the objective function, as well as maximization of an acquisition function and additional steps, as discussed in greater detail further below.

At step 503 the objective function is iteratively adjusted by repeatedly selecting one or more experiential genotype vectors in the plurality of experiential genotype vectors that maximize an acquisition function of the phenotype prediction model and updating the objective function based at least in part on one or more experimentally-determined phenotypic attributes corresponding to the one or more experiential genotype vectors. For example, this can be performed by modeling the plurality of experiential genotype vectors as a random forest and training the random forest using the corresponding experimentally-determined phenotypic attributes.

The process of step 503 is repeated until all of the experiential genotype vectors in the plurality of experiential genotype vectors are processed. Specifically, at step 504 a determination is made regarding whether there are additional experiential genotype vectors in the plurality of experiential genotype vectors that have not yet been processed. If so, then step 503 repeats. Otherwise, the training is terminated at step 505.

Once the phenotype prediction model is trained, it is necessary to evaluation genotypes within the solution space to determine the genotype that optimizes phenotype. However, in cases where the domain space of the objective function is huge and highly dimensional, the solution space of the optimization problem may become very difficult to define and explore efficiently. To solve this problem, the novel method and system disclosed herein utilizes a genotype generation model (also referred to as the "generative model" or the "generator model") to generate candidate genotypes. The derivation of this solution and use of the generative model in exploring the solution space is described in greater detail below.

Derivation of the Proposed Solution

In different areas, there is interest in designing and optimizing systems or processes so as to optimize a set of its properties or responses. Defining $f(\bullet)$ as the objective function of the optimization problem and $x \in \chi$ the domain of the system, then this can be expressed as follows.

$$\operatorname*{argmin}_{x \in \chi} f(x)$$

Generally, optimization problems are subject to some circumstances or constraints on the system that limits the region of feasible solutions. Although in some cases it's difficult to know the specific rules that define this solution space, the above optimization problem can be reformulated as $$\operatorname*{argmin}_{x_s \in X_b} f(x_s) \quad\quad 1.1$$

where $\chi_s \subseteq \chi$ denotes the solution space, or the set of all feasible solutions.

Applicants discovered a method that solves this optimization problem when:

The objective $f(\bullet)$ is a black-box function and the feasibility of obtaining evaluations may be restricted by budget constraints of different types: computational, temporal, economic, or others; and/or Some of the fundamental restrictions of the optimization problem that describe the solution space may be non-trivial to define.

Sampling Feasible Solutions

SMBO methods consider the optimization of an acquisition function to obtain candidates (new samples from the solution space to be tested). Some Bayesian Optimization approaches use quasi-Newton methods such as BFGS or L-BFGS, which explore the solution space starting from some initialization points to optimal values of the surrogate function by following the direction of an approximate gradient. Most of these methods require to specifically define the restrictions that describe the solution space. Other methods generate random samples (or alternatively, samples are selected from all possible candidates by heuristic rules) to make massive evaluations of the surrogate function in order to search for optima. Those methods also require to explicitly define the restrictions that confine the solution space.

As explained previously, in cases where the domain space of the objective function is huge and highly dimensional, the solution space of the optimization problem may become very difficult to define. For example (herein "Example 1"), consider the case of designing a protein (a sequence of amino acids) so that its properties optimize a specific function $f(\bullet)$. This can be defined as an optimization problem which aims to find a set of amino acid sequences $x^*$ that optimize said function, subject to an unknown set of constraints, which define the space of feasible proteins. The dimensionality of the domain space (domain of $f(\bullet)$) is vast due to the immense number of possible amino acid sequences which is roughly given by $\Sigma_{l=s}^{e} N_{ca}^{l}$. Where i represents the length of a sequence within the range (s,e), and $N_{ca}$ the number of possible amino acids (21). The above number can be huge, but in practice only a small subset of these combinations actually constitute the solution space, given that not all those sequences of amino-acid letters are feasible proteins. Most of them are only hypothetical molecules that won't behave as natural proteins (may not be safe for any organism or even stable for certain temperature ranges, etc.) and almost all the restrictions that limits the solution space are unknown.

The applicant proposes a solution to deal with this type of immense and/or unknown solution spaces. This proposal uses a clever way to solve these optimization problems by learning from samples of the solution space. The distribution of those samples is approximated by means of a generator model G which is trained with samples that aren't necessarily directly related with the optimization task at hand.

These generator models come in many forms (Hidden Markov Models—HMIs, Variational AutoEncoders—VAEs, Generative Adversarial Networks—GANs, etc.), but usually, what all of these do is to model a certain probability distribution from which sample elements can then be sampled. Now, one way to have a generator model is to use a parametric function $G_{\theta_G} \equiv G$ with adjustable parameters $\theta_G$ such that:

$$x_g \sim G_{\theta_G}(z); z \sim \mathbb{P}_z$$

Meaning that elements $x_g$ can be sampled following distribution $G_{\theta_G}(z)$, where z represents latent random variables that distributes with a known distribution $\mathbb{P}_z$, and $\theta_G$ are the parameters that are fitted in such a way that the generator function learns to map from a latent space $\mathcal{Z}$ to the $\chi$ space, $G: \mathcal{Z} \to \chi$ following the modelled distribution $\mathbb{P}_s$.

Now, finding the parameters $\theta_G$ is a non-trivial task. Attaining an optimal configuration of them is in itself another optimization problem, that may be expressed as follows.

$$\theta_G^* = \operatorname*{argmin}_{\theta_G \in \Theta_G} D_M[P(G(z)), P(x_s)]; G(z) \sim \mathbb{P}_G, x_s \sim \mathbb{P}_s \quad\quad 1.3$$

Where $\mathbb{P}_G$ represents the probability distribution of the generator model taking as input a random variable $z \sim \mathbb{P}_z$, and $\mathbb{P}_s$ the probability distribution of the solution space $\chi_s$. $D_M$ is some measure of probability distribution distance (e.g., Kullback-Liebler), so in other words, optimization 1.3 searches for the optimum parameters $\theta^*_G$ such that both distributions become the same.

In practice, there are several ways of optimizing these parameters, which are mainly dependent on the type of generative model being implemented (e.g., HMM, VAEs or GANs). As explained in greater detail below, the optimization process usually works by adjusting parameters $\theta_G$ such that the generator's distribution $\mathbb{P}_G \equiv G_{\theta_G}(z)$, with $z \sim \mathbb{P}_z$, is able to model the distribution of a subset (of size) of elements from the solution space $\{x_{s_i}\}_{i=0}^{N}$, $x_{s_i} \in \chi_s$.

In "Example 1", this solution space could be represented by a subset of all real known protein sequences. These can be found in online public protein databases such as the "Worldwide Protein Data Bank". With these elements, the parameters of the generator model can be fitted to model the probability distribution of this much more compacted and tractable solution space by solving optimization 1.3. Then, this generator can be used within an SMBO process, and one could simply sample a set of "new" elements from this distribution, rank them according to an acquisition function and generate a list of "candidates" from the top scored samples to be evaluated on function $f(\bullet)$. Then, just as in any common SMBO approach, repeat this for each iteration of the optimization process of problem 1.1.

This approach is related to "Transfer Learning." In Deep Learning, this term refers to the improvement of learning in a new task through the transfer of knowledge from a related task that has already been learned. In the proposed method the generator model can be trained using a dataset that is not specific to the optimization task, the approach may be described as a way of applying Transfer Learning into SMBO. This relation implies the sharing of some interesting properties that comes from this kind of learning, like model reusability (e.g., protein Generator model can be applied to several distinct tasks that involves proteins) and the possibility to achieve successful results without the need of a huge number of task-specific samples.

Returning to FIG. 1, at step 102 a genotype generation model is trained based at least in part on a plurality of sample genotype vectors, the genotype generation model being configured to generate new genotype vectors.

Figure 7:
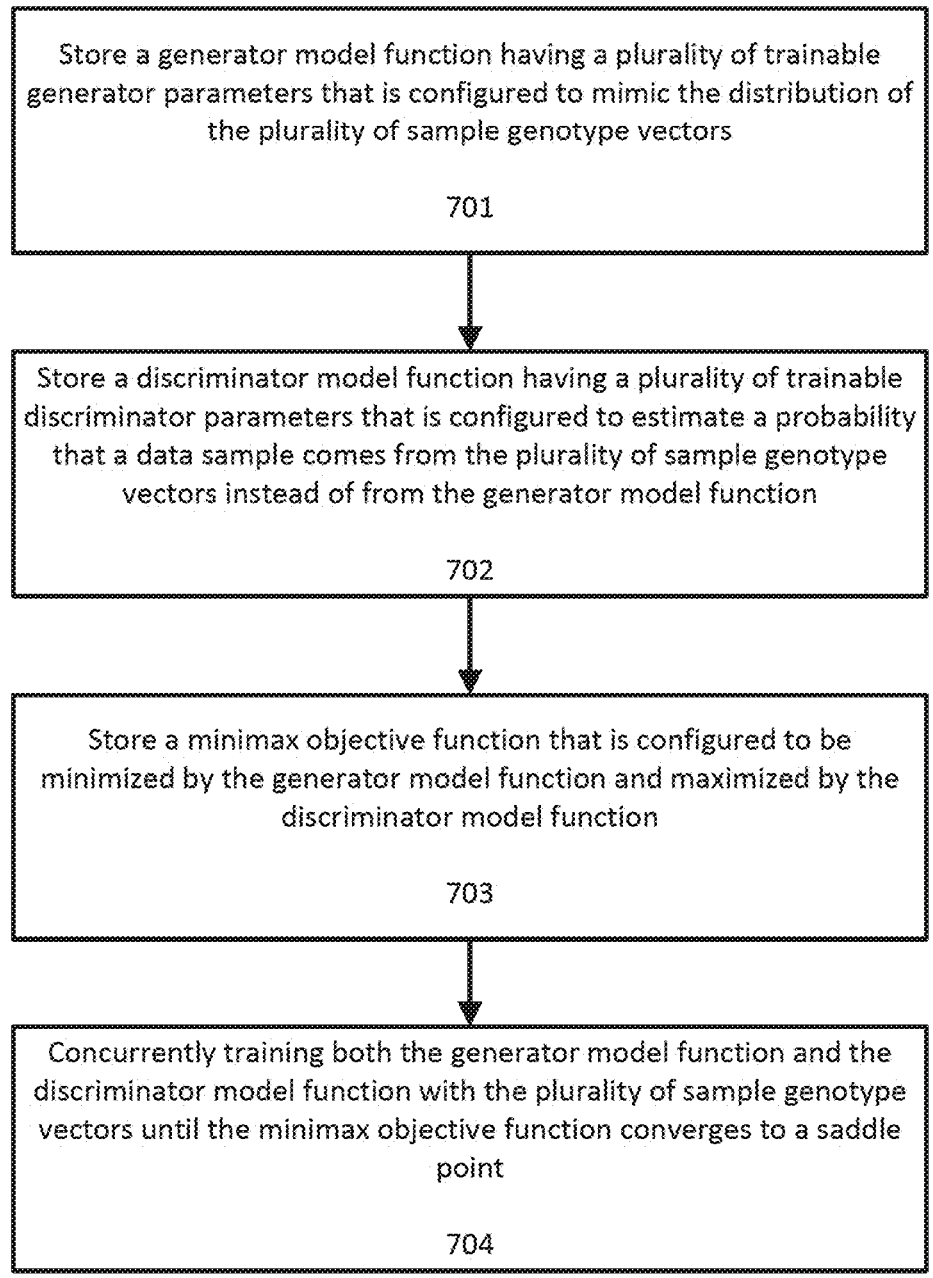
FIG. 7 illustrates a flowchart for training a genotype generation model based at least in part on a plurality of sample genotype vectors according to an exemplary embodiment.

FIG. 7 illustrates a flowchart for training a genotype generation model based at least in part on a plurality of sample genotype vectors according to an exemplary embodiment.

The genotype generation model can be a Generative Adversarial Network (GAN).

These networks seek to train a generative model from a set of input data. During training, the generator is encouraged to fit the probability distribution that characterizes this data set (i.e: the evidence probability distribution $\mathbb{P}_r$). Generally, the goal here is to use this trained generative model, to create new data with properties similar to the original set.

There are several mechanisms by which the probabilistic distribution of a data set can be estimated. One of them, for example, estimates through an adversarial training procedure with two functions, described below.

At step 701 a generator model function having a plurality of trainable generator parameters is stored. The generator model function is configured to mimic the distribution of the plurality of sample genotype vectors. The generator model function $G_{\theta_G}$, with trainable parameters $\theta_G$, mimics the distribution of the input data. For better readability the subindex "$\theta_G$" is omitted in this document, but it is implicit in the C function.

At step 702 a discriminator model function having a plurality of trainable discriminator parameters is stored. The discriminator model function is configured to estimate a probability that a data sample comes from the plurality of sample genotype vectors instead of from the generator model function. The discriminator model function $D_{\theta_D}$, with trainable parameters $\theta_D$, estimates the probability that a data sample comes from the real evidence distribution instead of from the synthetic generator distribution. For better readability the subindex "$\theta_D$" is omitted in this document, but it is implicit in the D function.

The adversarial training procedure involves training both of these functions/models concurrently. In this process, the generator model faces an "adversary": the discriminator model, trained to determine if a sample comes from the distribution of the generative model or from the distribution of the original real data.

In the traditional case, the weights/parameters of these networks are adjusted using optimization methods based on gradient ascent/descent in which an objective function is maximized/minimized.

However, instead of being trained as a traditional optimization problem, GANs are based on a "minimax game" and defined as a "zero-sum game" under the Game Theory approach. Under this perspective, one agent (a neural network) takes on the role of the Generator and another agent (another neural network) the role of the Discriminator. As explained below, a special objective function is used for the adversarial training process.

At step 703 a minimax objective function that is configured to be minimized by the generator model function and maximized by the discriminator model function. The minimax objective function is one in which one agent attempts to minimize the function and the other agent attempts to maximize it. In this case, the generator agent tries to minimize the objective function while the discriminator agent tries to maximize it:

$$\min_{\theta_G} \max_{\theta_D} \mathbb{E}_{x \sim \mathbb{P}_r}\left[\log D_{\theta_D}(x)\right] + \mathbb{E}_{\tilde{x} \sim \mathbb{P}_{\theta_G}}\left[\log(1 - D_{\theta_D}(\tilde{x}))\right] \quad \text{Equation 1.1}$$

Where x are the real samples coming from the evidence probability distribution $\mathbb{P}_r$, and are the synthetic generated samples coming from the generator distribution $\mathbb{P}_G$, which is defined by the function $G_{\theta_G}(z)$. being z the generator input, which is sampled from a simple noise distribution $z \sim p(z)$, such as a uniform or normal Gaussian distribution.

At step 704 both the generator model function and the discriminator model function are concurrently trained with the plurality of sample genotype vectors until the minimax objective function converges to a saddle point, which is a minimum with respect to the strategy of one player and a maximum with respect to the strategy of the other one.

Figure 8:
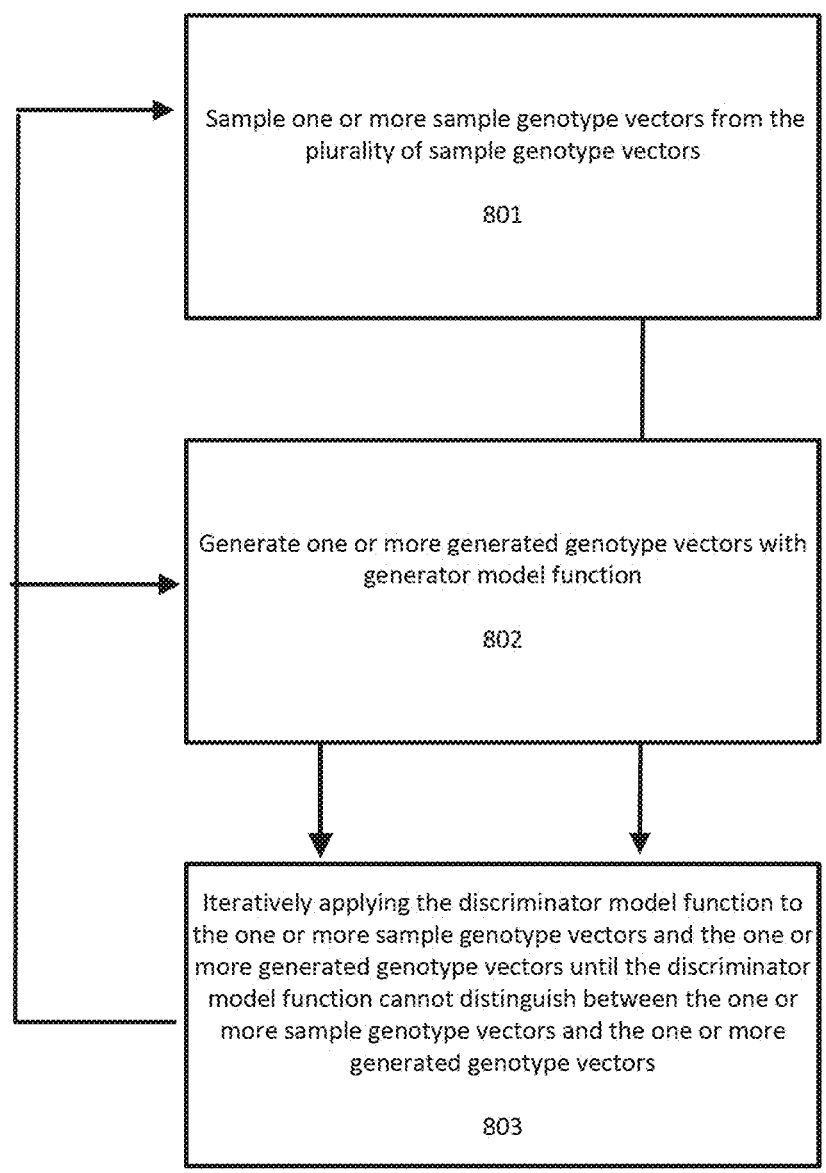
FIG. 8 illustrates a flowchart for concurrently training both a generator model function and a discriminator model function with sample genotype vectors according to an exemplary embodiment.

FIG. 8 illustrates a flowchart for concurrently training both a generator model function and a discriminator model function with sample genotype vectors according to an exemplary embodiment.

At step 801 one or more sample genotype vectors are sampled from the plurality of sample genotype vectors. Step 801 is repeated so that one or more sample genotype vectors are repeatedly samples from the plurality of sample genotype vectors.

At step 802 one or more generated genotype vectors are generated with generator model function. Step 802 is repeated so that one or more generated genotype vectors are repeatedly generated.

At step 803 the discriminator model function is iteratively to the one or more sample genotype vectors and the one or more generated genotype vectors until the discriminator model function cannot distinguish between the one or more sample genotype vectors and the one or more generated genotype vectors. As shown in FIG. 8, this step repeats after each iteration. Application of the discriminator model function alternates between the one or more sample genotype vectors and the one or more generated genotype vectors.

The training process alternates between the sample genotype vectors and the generated genotype vectors. For example, the sequence of steps shown in FIG. 8 can be 801→803→802→803→801→803 . . . etc. This allows the minimax objective function to reach the saddle point and terminate the training.

Figure 9:
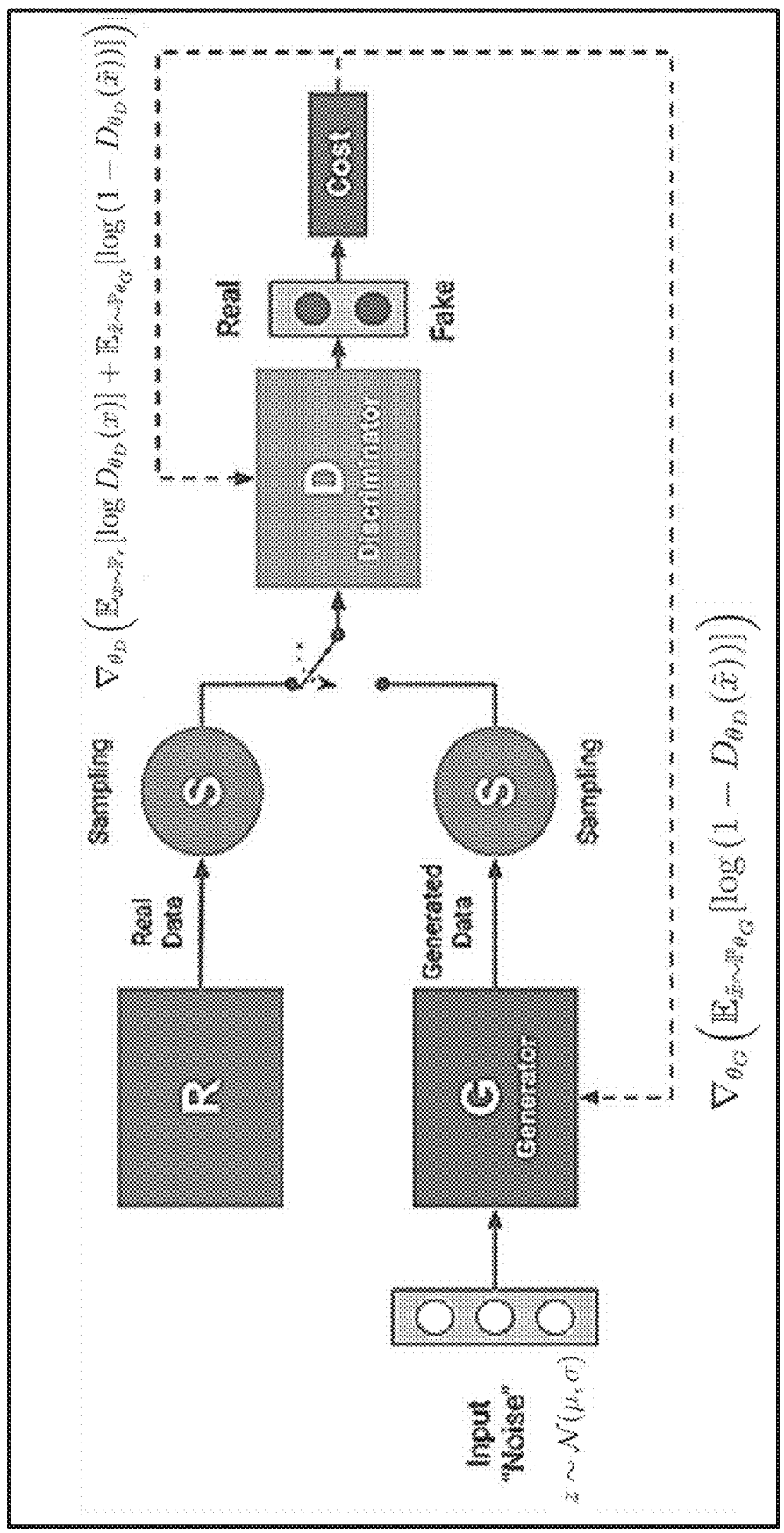
FIG. 9 illustrates a representative diagram of the adversarial training framework used for training a generative model according to an exemplary embodiment.

FIG. 9 illustrates a representative diagram of the adversarial training framework used for training a generative model according to an exemplary embodiment. The mathematical terms represent the gradients used to update the parameters of the generative and discriminative networks that are obtained from equation 1.1. The term with the symbol $\nabla_{\theta_D}$ corresponds to the gradient taken with respect to the parameters of the Discriminator and the term with the symbol $\nabla_{\theta_G}$ correspond to the gradient taken with respect to the parameters of the Generator.

As shown in FIG. 9, the Discriminator (D) is trained to "discern" (or classify) if the samples come from the Generator (G) or from the Real data (R). The Discriminator (D) models a cost function related to the probability of performing the classification correctly. This signal serves to iteratively adjust, through the gradients shown, both the Generator (G) and the Discriminator (D) parameters. The updates of the weights of both networks are done in shifts. The source of the samples to be discriminated is determined by the action represented by the "switch" at the center of the image. The sampling action is represented by the letter S. To sample from the distribution of the real data (R) an example is simply chosen randomly from said set. On the other hand, to sample from the generator, a random sample from a random noise source distribution is selected and then passed through the generator function G Under this approach, a GAN architecture converges when the Discriminator and the Generator reach a Nash Equilibrium. That is, the "game" ends when the optimization converges into a "saddle point" of the objective function, which is a minimum with respect to the strategy of one player and a maximum with respect to the strategy of the other one. This "competition" leads both players to optimize themselves until the generated samples are indistinguishable from the real samples (i.e., the generator distribution matches the real distribution).

Figure 10:
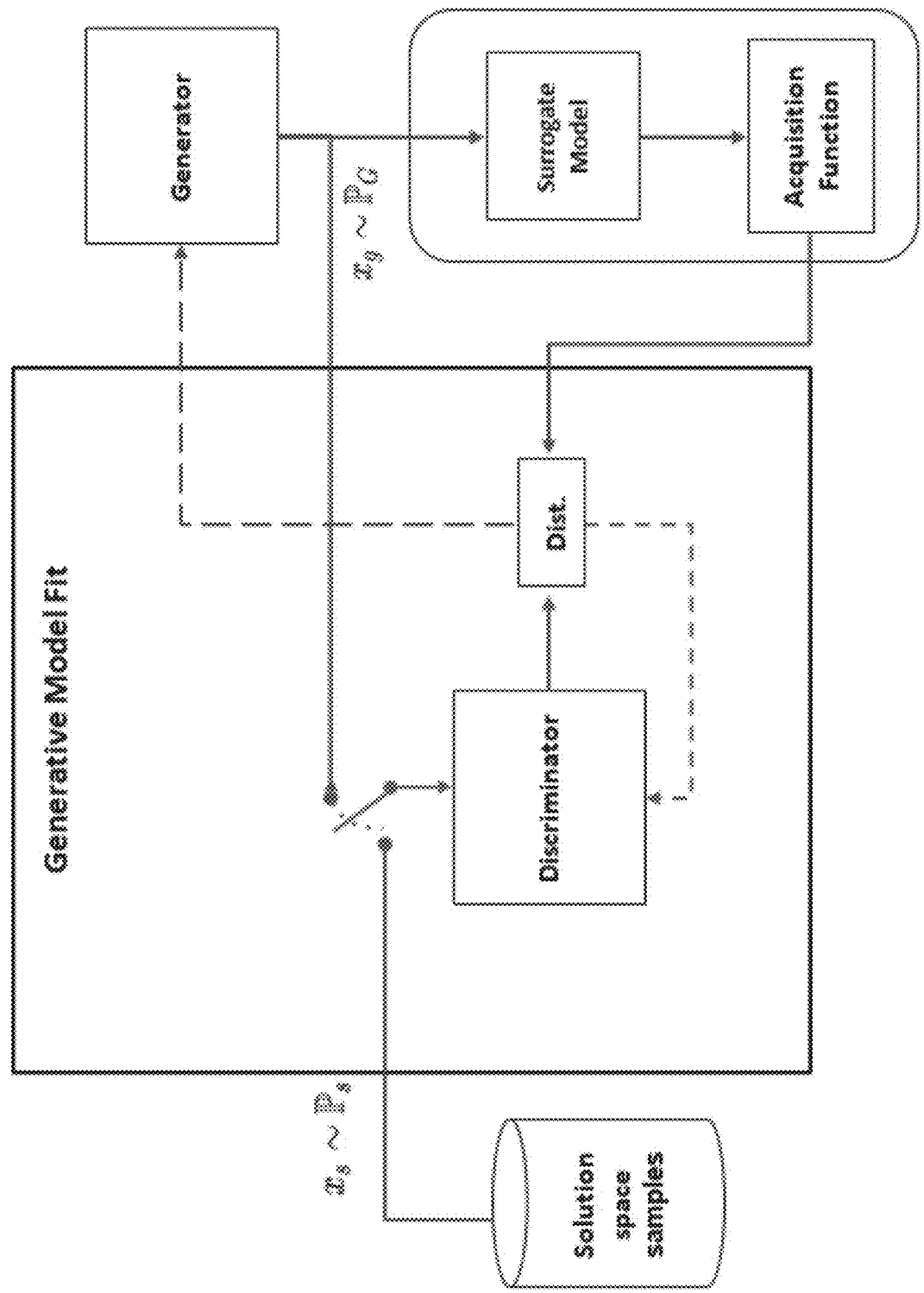
FIG. 10 illustrates a diagram of the parameter adjustment algorithm of the generative model according to an exemplary embodiment.

FIG. 10 illustrates a diagram of the parameter adjustment algorithm of the generative model according to an exemplary embodiment. The operation of the parameter adjustment algorithm is described in greater detail below.

The Wasserstein GAN with Gradient Penalty (WGAN-GP) was selected for generation. This approach is similar to the Wasserstein GANs, but to promote the "Lipschitz Condition" it uses a penalty term at the loss function instead of applying gradient clipping.

To adjust the Generator parameters, data that satisfies the problem's constraints should be used. Parameters are modified through an adversarial training framework. Here, 2 sets of parameters are optimized: Generator's ($\theta_G$) and Discriminator's ($\theta_D$) Once the training is finished, the generator should be able to model the probability distribution of the training dataset, so it is expected that synthetic samples obtained from this generator will satisfy the constraints of the problem.

FIG. 10 shows a diagram of the parameter adjustment algorithm of the generative model G, which is done under a modified version of the generative adversarial training framework. In particular, the discriminator D (or critic) is trained to estimate the (scaled) Wasserstein distance between the probability distribution of the generator $\mathbb{P}_G$ and the modelled probability distribution of the solution space $\mathbb{P}_s$, The generator is trained to minimize the Wasserstein distance estimate given by the critic. Additionally, to guide the generator to model the distribution that solves the optimization problem, feedback from the surrogate model $\hat{f}(\bullet)$ can be incorporated by adding a regularization term $\varphi(\hat{f}(\tilde{x}_g))$ to the generator cost function, and updating its parameters while the Discriminator's weights are fixed.

Figure 11:
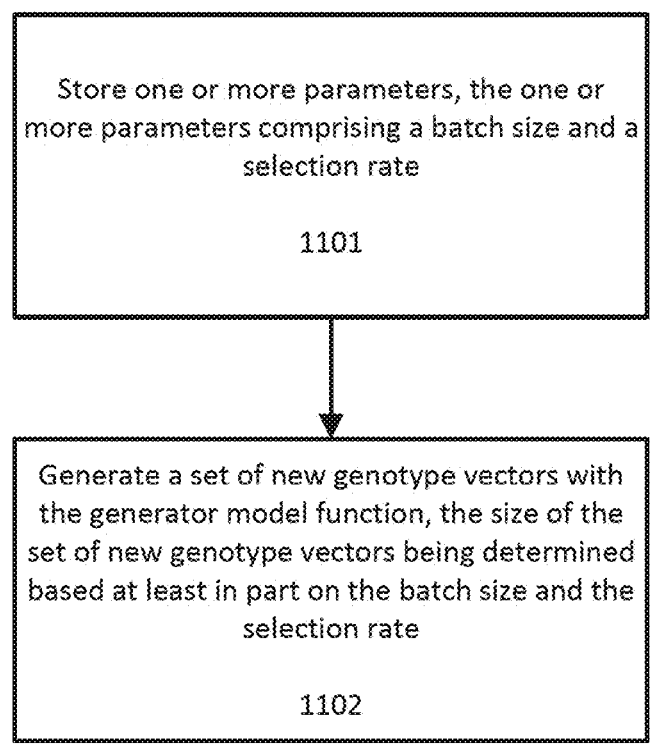
FIG. 11 illustrates a flowchart for generating a plurality of new genotype vectors with the genotype generation model according to an exemplary embodiment.

Returning to FIG. 1, at step 103 a plurality of new genotype vectors are generated with the genotype generation model. FIG. 11 illustrates a flowchart for generating a plurality of new genotype vectors with the genotype generation model according to an exemplary embodiment.

At step 1101 one or more parameters are stored, the one or more parameters including a batch size and a selection rate. A selection method is used to choose the most promising candidates resulting from the entire process to be evaluated by the Oracle (e.g., experimental testing). This selection method can be dependent on a number of different parameters, which can be provided by a user, set to some default value, or algorithmically determined. One of the parameters used can be the batch size, which describes the number of candidates $\underline{m}$ to be evaluated by the Oracle on each SMBO iteration. Another parameter can be the selection rate $s_r$, a value between 0 and 1 that denotes the size of the quantile of top candidates to be selected.

At step 1102 a set of new genotype vectors is generated with the generator model function. The size of the set of new genotype vectors (i.e., the quantity of new genotype vectors) can determined based at least in part on one or more parameters. In one example, the size of the set of new genotype vectors is determined based at least in part on the batch size and the selection rate. For example, when looking for top performing candidates, a total of $l=m/s_r$ elements can be sampled from (generated by) the generator model function of the genotype generation model. For the overall process, candidates can be selected following the constant liar approach, which stops after choosing era elements.

Returning again to FIG. 1, at step 104 the phenotype prediction model is applied to the plurality of new genotype vectors to generate a plurality of scores, the phenotype prediction model being configured to predict one or more phenotypic attributes of the new genotype vectors.

This step can include applying the objective function to the plurality of new genotype vectors to generate a plurality of prediction scores corresponding to the plurality of new genotype vectors. This step can also include applying an acquisition function of the phenotype prediction model to the plurality of new genotype vectors to generate a plurality of acquisition scores corresponding to the plurality of new genotype vectors. Additionally, this step can include determining an uncertainty score associated with each of the new genotype vectors in the plurality of new genotype vectors.

At step 105 a plurality of result genotypes are determined based at least in part on a ranking of the plurality of new genotype vectors according to the plurality of scores. This step can include ranking the plurality of new genotype vectors based at least in part on the plurality of prediction scores corresponding to the plurality of new genotype vectors and filtering out a percentage of the plurality of new genotype vectors below a predetermined ranking percentage to generate a plurality of result genotype vectors. The predetermined ranking percentage can be set by a user, set to some default value, based upon prior results or the particulars of the constraints or the experimental data set, or based upon implementation details of the particular predictive model type utilized.

At step 106 a result is generated based at least in part on the plurality of result genotypes, the result indicating one or more genetic constructs for testing. As discussed in greater detail below, this result can be a batch of single genetic constructs for testing or a combinatorial sequence that specifies multiple genetic constructs for testing. A user can optionally select whether they wish to receive a list of single genetic constructs or a combinatorial sequence.

Construct is used as a synonym of "candidate." Each construct represents a particular combination of genotype variants. For example, a combinatorial DNA design of complexity N, will lead to the assembly of N constructs.

The step of generating a result can include ranking the plurality of result genotype vectors based at least in part on an acquisition score associated with each result genotype vector and selecting one or more result genotype vectors in the plurality of result genotype vectors based at least in part on the ranking. This step can further include decoding the result genotype vectors to present the genotype information in a format that the user can understand and utilize or create in an experimental setting.

This step can be configured to select only the top-ranked result genotype vector. However, in the scenario where a user has specified that they would like a batch of results (genetic constructs for testing), the system must determine whether sufficient constructs have been generated and otherwise take the appropriate actions to update the model and generate additional constructs.

Figure 12:
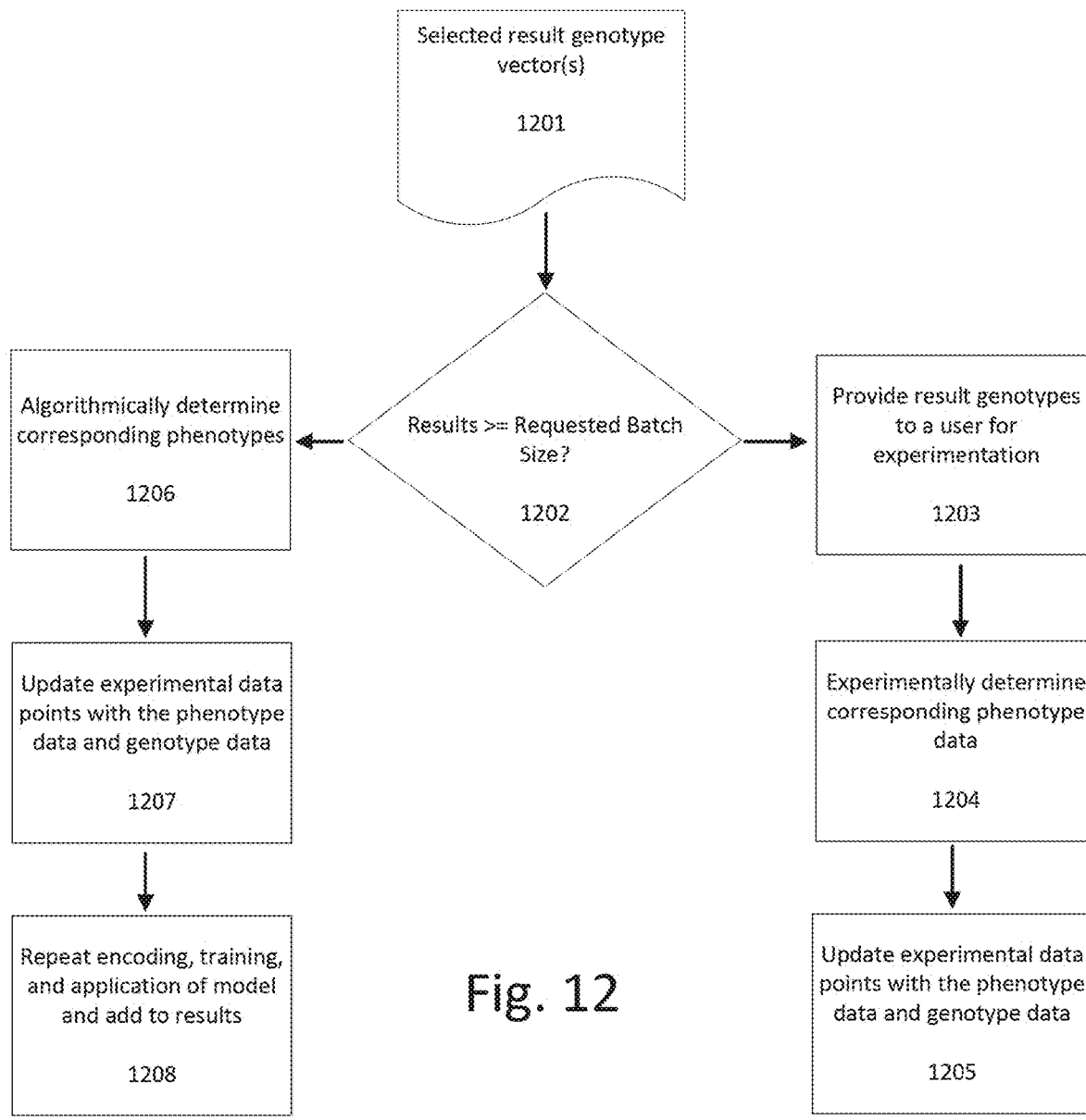
FIG. 12 illustrates a flowchart for updating the predictive model and determining whether to generate additional constructs according to an exemplary embodiment.

FIG. 12 illustrates a flowchart for updating the predictive model and determining whether to generate additional constructs according to an exemplary embodiment. As shown in FIG. 12, one or more selected result genotype vectors are the output of an initial application (evaluation) of the predictive model. At step 1202 it is determined whether the quantity of results is greater than or equal to the requested batch size.

If so, then at step 1203 the result genotypes corresponding to the selected result genotype vectors are provided to a user. At step 1204 the user experimentally determines phenotype data (i.e., Oracle determined phenotype measurements) corresponding to the result genotypes. The phenotype information can be determined by the Oracle by any of the methods discussed herein, such as experimental testing or mathematical modeling of real-world values. At step 1205 the experimental data points are updated with the genotype data of the results and the corresponding phenotype data. At this point, a further step can be performed of re-training the phenotype prediction model based at least in part on the one or more result genotype vectors, the corresponding phenotype information, and the one or more constraints discussed previously.

If at step 1202 the results are determined to be less than the requested batch size, then the process proceeds to step 1206. At step 1206 phenotypes corresponding to the selected result genotype vector are algorithmically generated. These generated phenotypes are fabricated values and can be generated in a variety of ways. One way to generate these phenotypes is use a phenotype prediction generated by the phenotype prediction model. Another way is to use the phenotype prediction minus the standard deviation of the prediction. Yet another way is to use some other linear combination of the predicted phenotype and its corresponding standard deviation. After the phenotypes are generated, the experimental data points are updated with the genotype data of the results and the corresponding phenotype data at step 1207.

At step 1208, the steps of encoding genotype information in the experimental data points, training the predictive model and optionally the generator model, generating new genotype vectors, applying the model, determining result genotypes, and generating a result are repeated with the updated experimental data points. This includes encoding genotype information in the updated plurality of experimental data points as an updated plurality of experiential genotype vectors, retraining the phenotype prediction model based at least in part on the updated plurality of experiential genotype vectors, the corresponding phenotype information, and the one or more constraints, optionally retraining the genotype generation model (if the same database of experiential genotype vectors are used as sample genotype vectors), applying the phenotype prediction model to remaining new genotype vectors in the plurality of new genotype vectors to generate an updated plurality of scores, determining an updated plurality of result genotypes based at least in part on an updated ranking of the remaining available genotypes according to the updated plurality of scores, and generating an additional result based at least in part on the updated plurality of result genotypes, the additional result indicating one or more additional genetic constructs for testing.

As shown in FIG. 12, regardless of whether the results are less than the requested batch size or greater than or equal to the requested batch size, a determination of phenotype data corresponding to the selected one or more result genotype vectors is made and the plurality of experimental data points are updated with the phenotype data and genotype data corresponding to the selected one or more result genotype vectors.

As discussed above, when a user requests a batch of single genetic constructs for testing, the predictive model can be applied to generate either one result genetic construct at a time or multiple genetic constructs per iteration. When multiple genetic constructs are determined per iteration, Applicant has discovered optimizations which reduce noise and improve computational efficiency. These optimizations are discussed in greater detail below.

Recommending Multiple Experiments (n_Batch Experiments)

In order to recommend a set of N candidates simultaneously, the optimization framework should provide several candidates per iteration step. For this, the disclosed method repeats the training and evaluation steps as much as needed, following the constant liar method. The actual predicted value of the untested candidate was used as fabricated value.

When maximizing the acquisition function within the liar approach, considering that usually the problem is restricted to a fixed number of possible designs, the most accurate way to find the optimal candidate is to evaluate the acquisition function in all designs. The drawback of this approach is that the number of possible designs could be huge, implying large computation times. This problem can be overcome by randomly sampling a fixed number of designs (10.000) from all possible designs for evaluation and selection of the optimal. However, this implementation may introduce an inconvenient noise factor into the formulation, making difficult to achieve consistent predictions between models trained with the same data. To speed up the algorithm without compromising accuracy, the applicants introduced a new heuristic rule: Instead of evaluating all possible designs or making a random subset of all candidates, a subset is built from the α% candidates with top predicted values. This limits the calculation time and ensures more consistency between different runs. The idea is to identify a that can define a list of top prediction candidates that will probably contain all selected candidates from the liar approach. We found that a value of α set to 60% worked on most of the experiments that we run. It should be noted that α value may change if a different number of selected candidates is required (we've set the limit to 100 candidates by default, as clients are rarely interested in having more). The use of the α rule helps to cut down by near a half the computation time without adding unnecessary randomness to the batch generation process.

FIG. 12 described the scenario where a user requested a batch single genetic constructs. However, a user can also specify that the step of generating a result should return a combinatorial design that is used to generate multiple genetic constructs.

Figure 13:
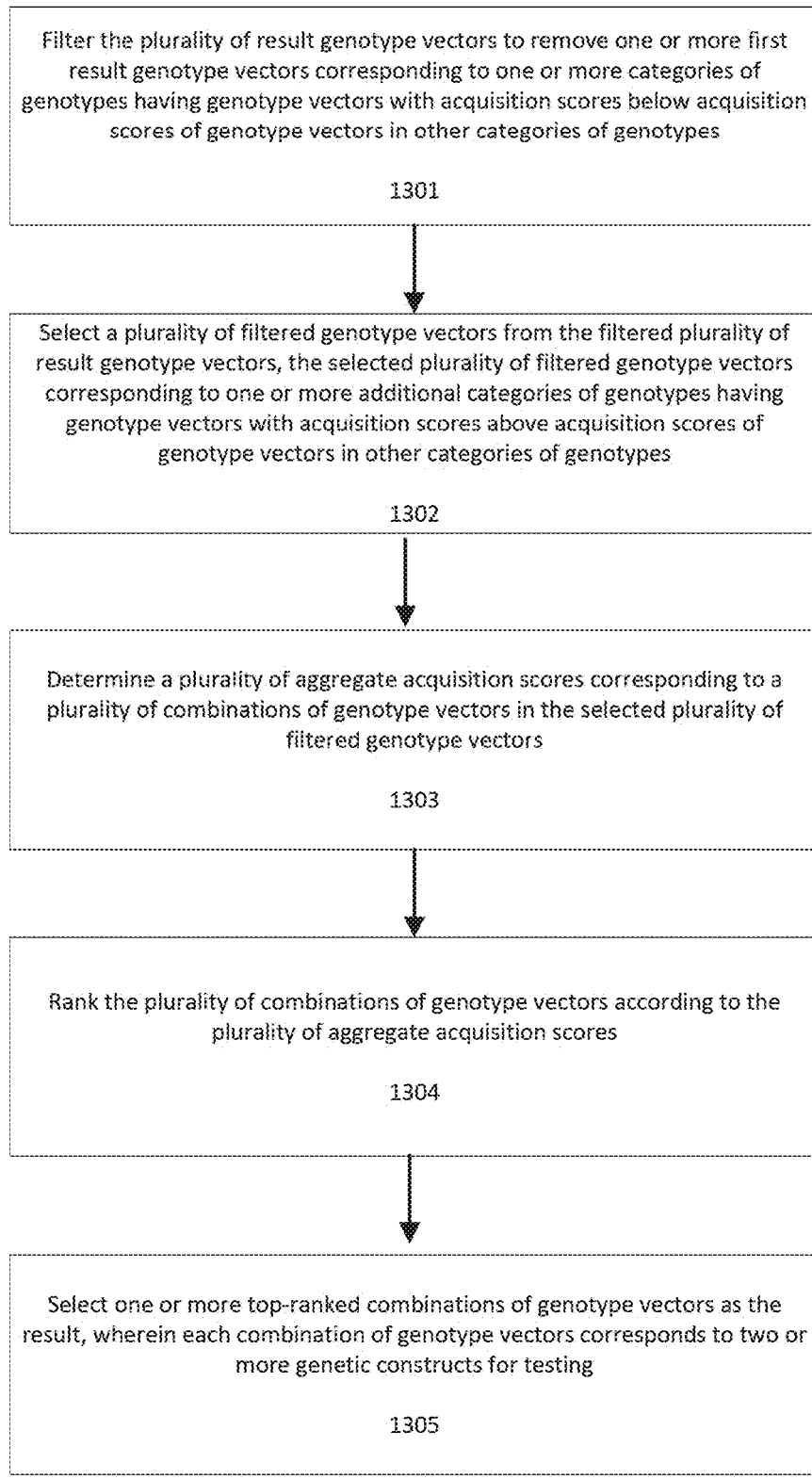
FIG. 13 illustrates a flowchart for generating a result based at least in part on the plurality of result genotypes when the user requests a combinatorial design according to an exemplary embodiment.

FIG. 13 illustrates a flowchart for generating a result based at least in part on the plurality of result genotypes when the user requests a combinatorial design according to an exemplary embodiment.

At step 1301 the plurality of result genotype vectors are filtered to remove one or more first result genotype vectors corresponding to one or more categories of genotypes having genotype vectors with acquisition scores below acquisition scores of genotype vectors in other categories of genotypes.

The word "category" is used herein as a synonym of genotype variant. For example, if each gene included in a design contains only one category (genotype variant), then the design would not be considered "combinatorial."

At step 1302 a plurality of filtered genotype vectors are selected from the filtered plurality of result genotype vectors, the selected plurality of filtered genotype vectors corresponding to one or more additional categories of genotypes having genotype vectors with acquisition scores above acquisition scores of genotype vectors in other categories of genotypes.

At step 1303 a plurality of aggregate acquisition scores are determined corresponding to a plurality of combinations of genotype vectors in the selected plurality of filtered genotype vectors.

At step 1304 the plurality of combinations of genotype vectors are ranked according to the plurality of aggregate acquisition scores.

Additionally, at step 1305 one or more top-ranked combinations of genotype vectors are selected as the result, each combination of genotype vectors corresponding to two or more genetic constructs for testing.

The process for generating a result based at least in part on the plurality of result genotypes when the user requests a combinatorial design corresponding to steps 1301-1305 is explained in greater detail below, with reference to specific examples.

Recommending Combinatorial Output

Applicant has developed a method for returning a reduced combinatorial design as output (instead of recommending a linear list of constructs). This can streamline the process of genotype optimization. The present section describes in detail a novel method to find the optimal combinatorial design out of the predictions over all single candidates.

When optimizing an organism by means of synthetic biology, some of the most common problems look as follows:

| Gene 1 | Gene 2 |
|---|---|
| Gene_1_variant_1 | Gene_2_variant_1 |
| Gene_1_variant_2 | Gene_2_variant_2 |
|  | Gene_2_variant_3 |

Table 1 illustrates an example of a combinatorial design. It contains 2 genes and each gene has a different number of possible variants. This specific example represents a biochemical reaction that depends on two enzymes of different kinds. Those enzymes are encoded as genes. The scientist has found 2 valid sequence alternatives for the first enzyme, and 3 options for the second gene.

Usually there is a set of bins or positions in a genetic design where, within each bin, there's a limited number of possibilities to choose from. In the example case, the first gene position or bin may have 1 from 2 different alternatives, while the second gene has 3 variants to choose from.

The data displayed at table 1 represents a combinatorial design. Usually the scientist is searching for the best combination of the variants and looks for the one with the highest production rate of a certain product. Given the above example, there are 6 possible solutions for the problem which are generated from the combinations of all variants. In the following table, each row represents one of these, also called as "single solutions" or constructs:

| Construct ID | Gene 1 | Gene 2 |
|---|---|---|
| 1 | Gene_1_variant_1 | Gene_2_variant_1 |
| 2 | Gene_1_variant_1 | Gene_2_variant_2 |
| 3 | Gene_1_variant_1 | Gene_2_variant_3 |
| 4 | Gene_1_variant_2 | Gene_2_variant_1 |
| 5 | Gene_1_variant_2 | Gene_2_variant_2 |
| 6 | Gene_1_variant_2 | Gene_2_variant_3 |

Table 2 illustrates a list of the 6 singular solutions/constructs associated with the combinatorial example shown in Table 1.

As it was noted before, the scientist is looking for a construct within a combinatorial design that maximizes a specific experimental measurement. This is the kind of candidate solution that SMBO methods provide. Single solutions. In this case, the scientist should build each of the proposed candidates, make experiments, evaluate them in the lab, feed the algorithm and continue with the DBTL cycle until criteria is met. This process works fine, however there is room for improvement.

One of the shortcuts that biochemistry allows scientists to do is to generate all of the constructs from a combinatorial design at once, with just a few biochemical reactions. This is not free, as sequencing and labelling all combinations from a huge combinatorial design can be very hard, but the applicants have found that in some cases the algorithm can take advantage of this property and streamline the optimization process.

As scientists can find interesting to work with combinatorial designs of limited complexity (instead of working with a huge combinatorial design or lists of isolated constructs) the Combinatorial Solution option was implemented to suggest a "reduced" combinatorial design rather than a list of single candidates. This approach can allow the user to test hundreds or thousands of different meaningful designs at each optimization step, instead of just a few. Depending on the nature of the problem, this kind of solution may reduce experimental costs, hence increasing the number of samples tested on each iteration and improving the achieved optima. Also it may help to reduce experimentation time.

The Combinatorial Output is a new step in the optimization process that runs (optionally) after all single candidates are evaluated. Considering that part of this method can be computationally demanding, the applicants created a first filtering stage, where some categories are discarded by using some heuristic rules, and then a fine-tuning stage where all the remaining categories are studied in detail.

The first stage uses two pre-filter methods. The first one finds, for each bin the worst performing categories where all its singular construct's scores are below the ones of the other categories. After identifying these low scored categories, the associated singular constructs are removed from the candidates list. Then, the second pre-filter is applied, which starts building a combinatorial design by collecting the best top 'N' performing categories according to a ranking based on the acquisition value of their corresponding singular candidates. The number 'N' of collected categories will be given by a pre-determined combinatorial complexity threshold. The combinatorial complexity is given by the product formula below. Where $n_{bi}$ and $n_{bf}$ correspond, respectively, to the initial number of categories and the final number of categories of bin 'b'. The final number of categories of each bin is pre-determined by the user based on her needs.

$$\text{Combinatorial Complexity} = \prod_{b=1}^{|b|}(n_{bi} \text{ choose } n_{bf})$$

Higher combinatorial complexity means wider exploration space, increasing the chances of attaining global optima, but at the cost of a higher computational complexity. The result of the first stage will then be another combinatorial design, with lower complexity (due to the pre-filtering), that will be used as the input for the second stage.

The second stage (fine-tuning) is an exhaustive search that calculates a score for all possible combinatorial candidates of limited complexity that can be derived from the input combinatorial design (the one coming from the first stage). The implementation of this method is not trivial as complexity scales quickly with the size of the input and resources should be managed carefully. In what follows from this section, in addition to describing in detail the strategy approached to find the optimum, the limitations of the algorithm are studied. The latter allow to define the combinatorial complexity threshold to be used in the filtering stage.

The fine-tuning stage basically calculates an aggregated score from the acquisition values of every single construct that belongs to each combinatorial candidate. The user may select the score to be the average acquisition value of the constructs, or the maximum, or in fact, any other combination of the statistics of the acquisition values (s.a: mean, standard deviation). Based on this score, the best combinatorial designs are stored during execution and returned to the user after evaluating all combinatorial candidates.

To better understand what the fine-tuning stage does, consider the acquisition function results of the constructs from the previous example:

| Construct ID | Gene 1 | Gene 2 | Acquisition score |
|---|---|---|---|
| 1 | Gene_1_variant_1 | Gene_2_variant_1 | 2.12 |
| 2 | Gene_1_variant_1 | Gene_2_variant_2 | 3.01 |
| 3 | Gene_1_variant_1 | Gene_2_variant_3 | 4.02 |
| 4 | Gene_1_variant_2 | Gene_2_variant_1 | 3.11 |
| 5 | Gene_1_variant_2 | Gene_2_variant_2 | 3.98 |
| 6 | Gene_1_variant_2 | Gene_2_variant_3 | 5.03 |

Table 3 illustrates acquisition values for each construct within a hypothetical (big) combinatorial design. Acquisition values will be combined to calculate the scores for each (reduced) combinatorial candidate.

Depending on the requirements, the user can set the final desired complexity or, alternatively, the maximum number of categories per bin of the output combinatorial design. This will determine the number of possible different constructs that can be derived from the resulting combinatorial design and, also, define the set of all combinatorial candidates to be ranked. For instance, following our example case, if the scientists wants a combinatorial output with $n_f=2$ final categories per bin, the number of constructs that can result from that output is $s_f=(n_f)^b=4$, and the resulting candidates will be the ones listed in the following table. This table also shows the calculation of candidates' scores:

| Combinatorial Design ID | Gene 1 | Gene 2 | Single constructs ID | Aggregated Score (average) |
|---|---|---|---|---|
| 1 | Gene_1_variant_1 | Gene_2_variant_1 | 1, 2, 4, 5 | 3.06 |
|  | Gene_1_variant_2 | Gene_2_variant_2 |  |  |
| 2 | Gene_1_variant_1 | Gene_2_variant_1 | 1, 3, 4, 6 | 3.57 |
|  | Gene_1_variant_2 | Gene_2_variant_3 |  |  |
| 3 | Gene_1_variant_1 | Gene_2_variant_2 | 2, 3, 5, 6 | 4.01 |
|  | Gene_1_variant_2 | Gene_2_variant_3 |  |  |

Table 4 illustrates combinatorial candidates for the example problem with their respectives scores.

The Combinatorial Solution method returns the top ranked combinatorial designs according with the aggregated scores. The user may build all the associated constructs from one or more proposed solutions and evaluate them. After that, she can feed the model with constructs' data and generate a new set of combinatorial or singular candidates.

From the example above, this problem (scoring all combinatorial candidates) seems very simple. However, the number of combinatorial candidates explodes with big combinatorial designs so, from the computational complexity perspective, the implementation of this solution provides many challenges.

A typical strain optimization problem contains b=6 bins and a number of original categories per feature $n_O=7$. The number of all single solutions will be given by the expression:

$$s=(n_O)^b$$

which here takes the value s=117,649.

If the user wants to reduce to $n_f=2$ final categories per feature, the number of combinatorial candidates will be given by the following expression:

$$c=(n_O \text{ choose } n_f)^b$$

which in this case takes the value c=85,766,121 combinatorial candidates (and increases quickly with bigger values of $n_O$)

One way to achieve massive calculations these days is by using graphical processing units (GPUs) to take advantage of their parallel processing capabilities. To do so is important to find a valid representation of the problem that suits the available tools to exploit hardware's parallelism. With that objective, the following definitions were made:

$S \in B^{s \times k}$: Is the binary matrix of single solutions. Each row represents a single solution and each column represents one of k total categories. Each component will have a value of 1 if the category is present in the construct and 0 if not.

$T \in R^s$: Is the target vector. It contains the float valued scores predicted for each single design.

$C \in B^{c \times k}$: is the binary matrix of valid combinatorial solutions. Each row represents a combinatorial design and each column represents one of k total categories. Each component will have a value of 1 if the category is present in the design and 0 if not.

Considering that when a single construct is contained by a combinatorial design they will share components with value "1" in b (number of bins) dimensions, we can define the Membership matrix $M \in B^{c \times s}$ as:

$$M_{i,j} = \begin{cases} 1 & (C \cdot S^T)_{i,j} \geq b \\ 0 & \sim \end{cases}$$

that will be valued "1" in position i,j if the construct j can be obtained from the combinatorial design i.

After constructing the Membership matrix M, the single scores associated with each combinatorial design can be obtained by means of boolean indexing in the target vector T. With those acquisition values, the combinatorial aggregated score can be easily calculated.

A more formal expression for the average acquisition score specifically, denoted as the vector $A \in \mathbb{R}^c$ for all combinatorial candidates is given by:

$$A = \frac{1}{c_f} M \cdot T$$

where $c_f$ is the number of singular constructs associated with a combinatorial candidate. This value is equal across all valid combinatorial candidates as they were selected to have the same complexity.

The above formulation was implemented for GPU execution. It has to be run in batches, as the calculations may not fit in the processor's memory. Scores are calculated using partitions $\underline{C} \in B^{bs \times k}$ of combinatorial candidates, where bs is the batch size. The best scored designs are stored during the process. The following table shows the execution times of the search of best scores, given the list of scores for the singular constructs (tests were run on an AWS p2.xlarge machine instance):

| $n_o$ | b | Number of singular candidates s | Number of reduced combinatorial samples c ($n_f = 2$) | time [h] | Batch size used (bs) |
|---|---|---|---|---|---|
| 3 | 6 | 729 | 729 | 0 | 4096 |
| 4 | 6 | 4096 | 46656 | 0 | 4096 |
| 5 | 6 | 15625 | 1000000 | 0 | 4096 |
| 6 | 6 | 46656 | 1.1E+07 | 0.2 | 4096 |
| 7 | 6 | 117649 | 8.6E+07 | 2.3 | 2048 |

Table 5 illustrates computation times of the combinatorial solution step. Results are shown for different number of categories per bin of the original combinatorial design $n_O$.

As shown on Table 5, for high values of c, calculations can become very time consuming. Also, matrix S increases its size with $n_O$, which may become high enough to not fit into memory. For this reason, the reach of the fine-tuning stage has to be limited to available resources. Using table 5, the applicants set the combinatorial complexity threshold to 8.6E+07, considering the machines that are currently available in their environment, and the amount of time their users are willing to spend on this calculation.

Figure 14:
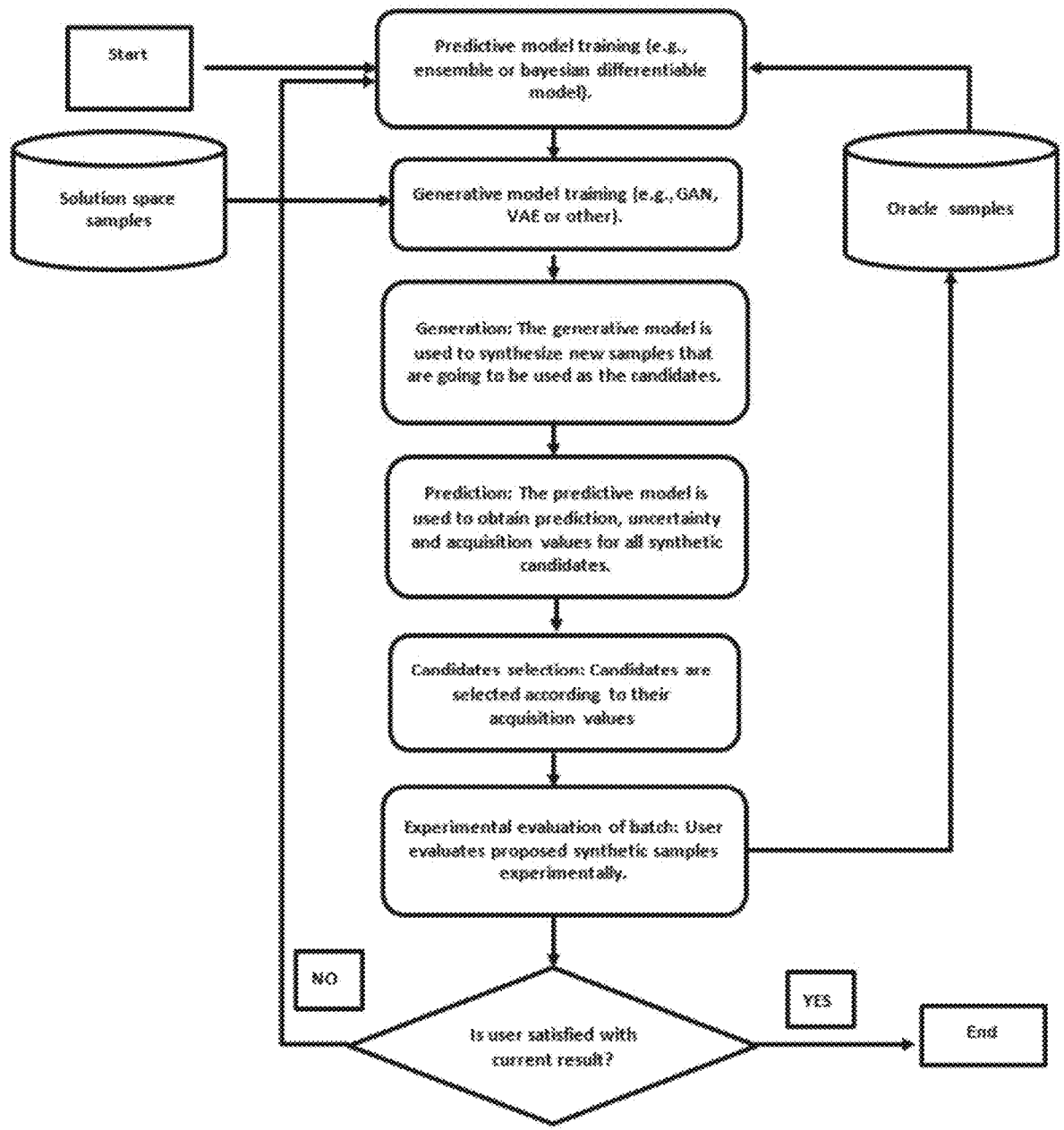
FIG. 14 illustrates high-level flowchart of the methods and system components described herein according to an exemplary embodiment.

FIG. 14 illustrates high-level flowchart of the methods and system components for efficiently optimizing a phenotype with a combination of a generative and a predictive model described herein according to an exemplary embodiment.

The applicant has discovered a black-box optimization method and system for efficiently optimizing a phenotype with a combination of a generative and a predictive model. The disclosed methods and systems are based on SMBO and can be used to deal with immense domain spaces. Some of the terms used in the above-described sections and throughout this application are explained in greater detail below.

Parametric functions $$G_{\theta_G}: \mathcal{Z} \to \mathcal{X}$$

(generative model) and $$\tilde{f}_{\theta_f}: \mathcal{X} \to \mathbb{R}$$

(predictive model (a.k.a surrogate)) are defined with trainable parameters $\underline{\theta_G}$ and $\underline{\theta_f}$ respectively, being $\mathcal{Z} \subseteq \mathbb{R}^{\underline{D_z}}$ a given latent space with dimension $\underline{D_z}$ and $\chi \subseteq \mathbb{R}^{\underline{D_x}}$ the optimization problem's solution space with dimension $\underline{D_x}$.

A "Selection Method" is used to suggest a list of candidates based on a set of criteria. These criteria may be non-trivial depending on the trade-off between exploration and exploitation desired. As discussed earlier, the Selection Method can be based on the parameters of batch size and a selection rate. The Selection Method can also be based upon the rankings or scores of the candidates/genotype vectors.

An "oracle" represents the "black-box" function $\underline{f}: \chi \to \mathbb{R}$. As discussed earlier, the oracle can correspond to the results of experimental testing in a lab or mathematical modeling of real-world behavior.

Two sets of data are also defined: a labelled set $\underline{D_f} = \{(\underline{x_{f_i}}, \underline{y_{f_i}})\}_{i=0}^{N_f}$, with $\underline{x_{f_i}} \in \underline{\chi_f} \subseteq \chi$ and with $\underline{y_{f_i}}$ a possible noisy measurement of the black-box function for input $\underline{x_{f_i}}$, used to adjust parameters $\theta_f$ of the predictive model and another set $\underline{D_g} = \{\underline{x_{g_i}}\}_{i=0}^{N_g}$ (not necessarily labeled) with $\underline{x_{g_i}} \in \underline{\chi_g} \subseteq \chi$ used to adjust parameters $\underline{\theta_G}$ of the generative model.

With the above terms, the disclosed method that optimizes problem 1.1 is described by the following steps:

Step 1: Adjust the surrogate/predictive model $\underline{\tilde{f}}$ using the labelled dataset $\underline{D_f}$ to adjust parameters $\underline{\theta_f}$ by optimizing problem 1.2.

Step 2: Adjust the generative model $\underline{G}$ using generator's dataset $D_g$ to adjust parameters $\underline{\theta_G}$ by optimizing problem 1.3.

Step 3: Generate $\underline{k}$ samples $$\{x_{g_i}\}_{i=1}^{k} \sim \tilde{\mathbb{P}}_g$$

and evaluate them using $\tilde{f}_{\theta_f}(\bullet)$.

Step 4: Use the "Selection Method" method to choose the top $\underline{m \leq k}$ samples considering the values provided by the acquisition function.

Step 5: Evaluate $\underline{m}$ selected samples with the "oracle".

Step 6: Readjust the parameters of the predictive model $\underline{\tilde{f}}_{\theta_f}$ is considering the new information obtained from the oracle, using $\underline{N_f + m}$ labelled samples.

Step 7: Repeat from point 3 until number of desired genotypes obtained.

As stated earlier, the overall process is shown in FIG. 14. Referring to FIG. 14, the iterative process begins with a set of initial experimental database of data points used to train the predictive model. The initial experimental database of data points can then also be used to train the generative model. Alternatively, a different data set, such as a sample database, can be used to train the generative model. The training data selected for the generative model can be used to improve/refine results produced by the system by selecting training data which is more likely to contain an optimal genotype. Applicant notes that the order of training is unimportant, and that the predictive and generative model can be trained either together/jointly or taking turns.

Continuing to refer to FIG. 14, the generative model is then used to synthesize a set of new data points known as "candidates" that are evaluated and ranked using the prediction and uncertainty of the predictive model. Subsequently, the top ranked candidates are tested experimentally using these results to update the experimental database (Oracle samples). Optionally, the solution space dataset can be updated. The cycle shown in FIG. 14 is repeated until satisfaction of criteria/optimal results are obtained.

The steps described above can be implemented in various ways. For example, in one implementation, both the Surrogate model and the Generator model are neural networks. In this case, the adjustment of both models' parameters is performed using gradient-based optimization techniques, like stochastic gradient descent (ascent), through which a loss function is minimized (maximized). The optimization process can be streamlined if the available data is used to adjust the parameters of both models before starting.

The disclosed SMBO methods can use as surrogate any machine/deep learning model that can manage numerical and categorical inputs, and can be configured to output an estimation of uncertainty as well as a prediction value. This includes most of ensemble-based algorithms. For example, Random Forests, XGBoost and others; also, Bayesian approaches can be used, like Bayesian Networks, etc. Additionally, includes methods based on Deep Ensembles, Bayesian Deep Learning, etc. For example, an implementation can use a sklearn implementation of Random Forest Regressor (RF) as the surrogate model.

The disclosed methods can use many different acquisition methods as scoring functions. The Expected Improvement was selected for the current implementation. However, the disclosed method is not limited to it, and any other score that can be used within the disclosed SMBO framework could also be applied.

Figure 15:
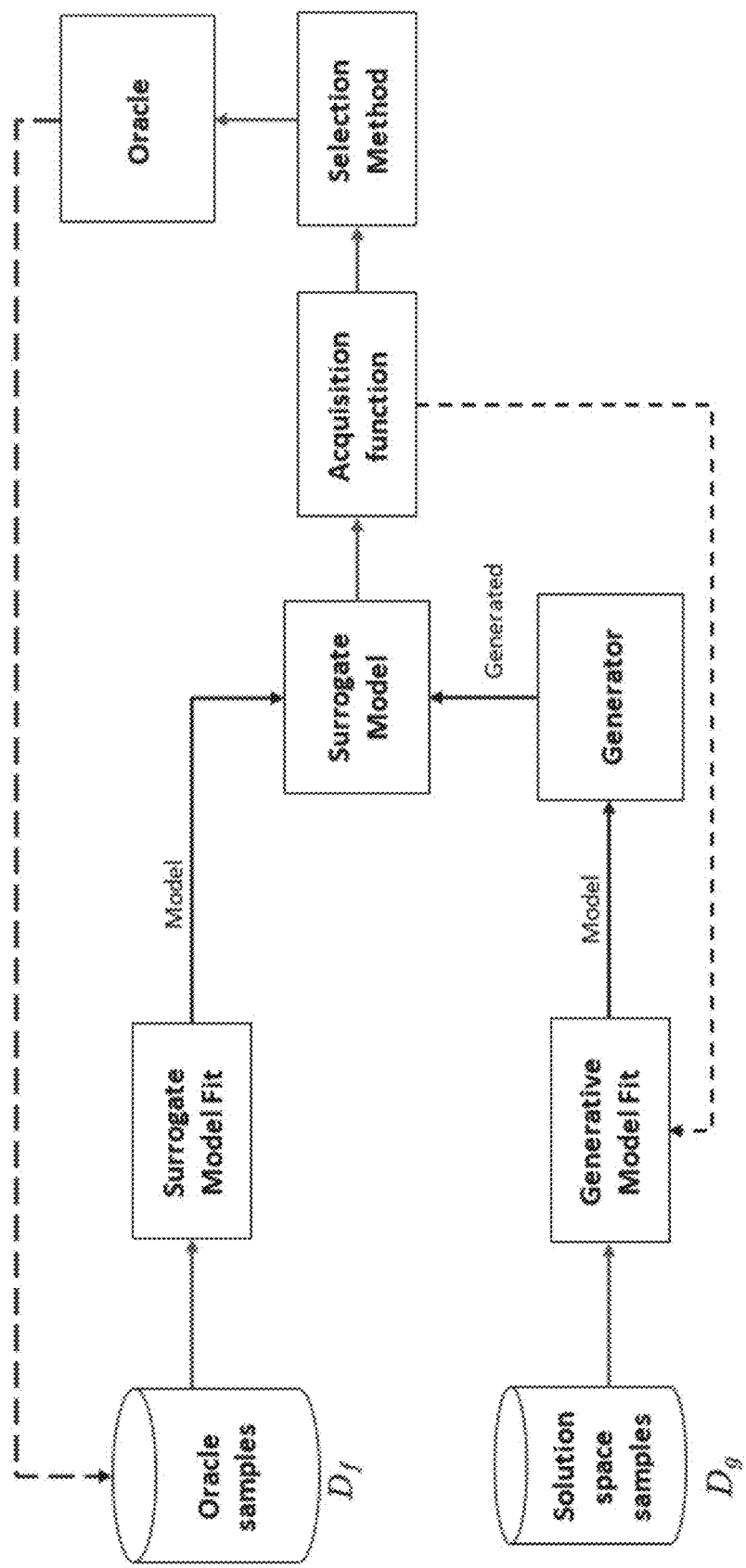
FIG. 15 illustrates the components and process flow of the system for efficiently optimizing a phenotype with a combination of a generative and a predictive model according to an exemplary embodiment.

FIG. 15 illustrates the components and process flow of the system for efficiently optimizing a phenotype with a combination of a generative and a predictive model according to an exemplary embodiment. FIG. 15 shows in greater detail the components used to carry out multiple steps shown in FIG. 14.

As shown in FIG. 15, the generative model is trained with samples obtained from the solution space. This training process may also include feedback results from the acquisition function (see additional features discussed below). The surrogate function is trained using data processed by the oracle. Once the generator and the surrogate are trained, the generator is used to generate synthetic samples and each synthetic sample is scored by the acquisition function. After that, a Selection Method chooses the best scored candidates and suggests them to be evaluated by the Oracle, evaluated samples may be added to the oracle dataset in order to be considered in the next SMBO iterations.

There are various additional features and additional steps, some of which are described above, that can be utilized as part of the disclosed method, apparatus, and computer-readable medium for efficiently optimizing a phenotype with a combination of a generative and a predictive model. These additional features and additional steps (referred to as extensions) will now be described in greater detail below.

Using Embeddings to Use a Surrogate that Evaluates Samples in Latent Space Domain The SMBO strategy supports both categorical and numerical data types as inputs. However, depending on the surrogate model used, these inputs might need to be encoded into a different representation. For instance, when working with genetic sequences, which in their original form correspond to sequences of categorical symbols or tokens (e.g., the four nucleotides A, T, G, and C), one would likely use a different representation (which we generally call "embeddings") so to use them to feed a model (e.g one-hot representation instead of strings) or even reduce dimensionality (as these sequences can be huge) and standardize the dimensions of model's input (considering that genetic sequences may have different lengths).

An embedding may be constructed by training deep learning models on vast amounts of data. The volume of datasets used in SMBO are sometimes too low to be useful for building an effective embedding, so these encoder models tend to be pre-trained on external much larger datasets which exploits the advantages of "Transfer Learning", a methodology that allows a model to apply knowledge from a large dataset to a more specific task.

Through embedding techniques, the input data can be represented as numerical vectors that lie in a multidimensional space. These numerical vectors encode sequence information capable of making relationships in the multidimensional space that have some physical properties (e.g., biochemical properties) This dense representation in a continuous space makes it possible for the model to have access to richer information about the sequences that allows the model to better identify, extract and exploit the relationships between them.

When using these embeddings, the inputs of the surrogate are continuous. Hence, the SMBO approach might take advantage of this and use a surrogate model where optima can be obtained through newton or quasi-newton methods (such as Deep Ensembles, Deep Gaussian Processes, Bayesian Networks or other Bayesian approaches).

A useful additional feature of the disclosed method and system is to encode the original domain into a latent space. This can help to reduce the dimensionality of the generator and surrogate models. The approach to encode samples can vary and depends upon the nature of the solution space. In the case of using a learnable embedding, samples from $D_g$ or another dataset could be used for training. An overview of this approach is shown in FIG. 16.

Figure 16:
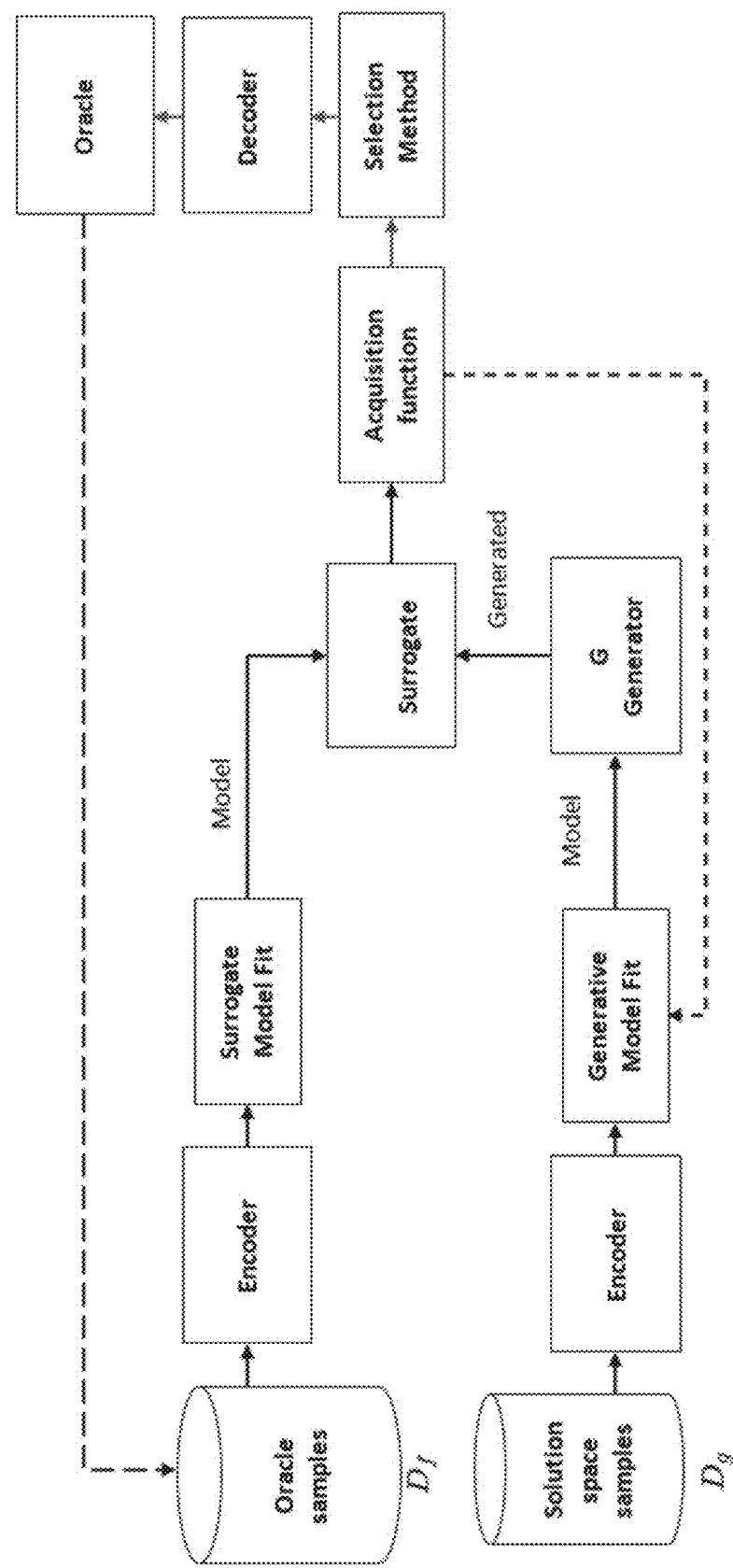
FIG. 16 illustrates the components and process flow of the system for efficiently optimizing a phenotype with a combination of a generative and a predictive model with embedding according to an exemplary embodiment.

FIG. 16 illustrates the components and process flow of the system for efficiently optimizing a phenotype with a combination of a generative and a predictive model with embeddings according to an exemplary embodiment. This extension of proposed framework uses embeddings. With this extension, instead of using the original domain space, the generator and surrogate models are trained using encoded versions of the samples instead. Encoder and Decoder modules are used to map from the solution space to a latent space and vice versa.

A reduced version of this can be applied when using an encoder/decoder architecture as a generator. This is the case of some Autoencoders, Variational Autoencoders, some GANs architectures and others. In these cases, the generative model can be divided into three separate modules: the first module is the encoder, which translates samples from the domain to the latent space, the second module is the decoder, which maps samples from the latent space to the problem domain, and the third module represents the sampling process from the latent space $\mathcal{Z}$.

When a generative model satisfies the above property, adjustments can be made to the architecture with embeddings to reduce models' complexity. These modifications are shown FIG. 17.

Figure 17:
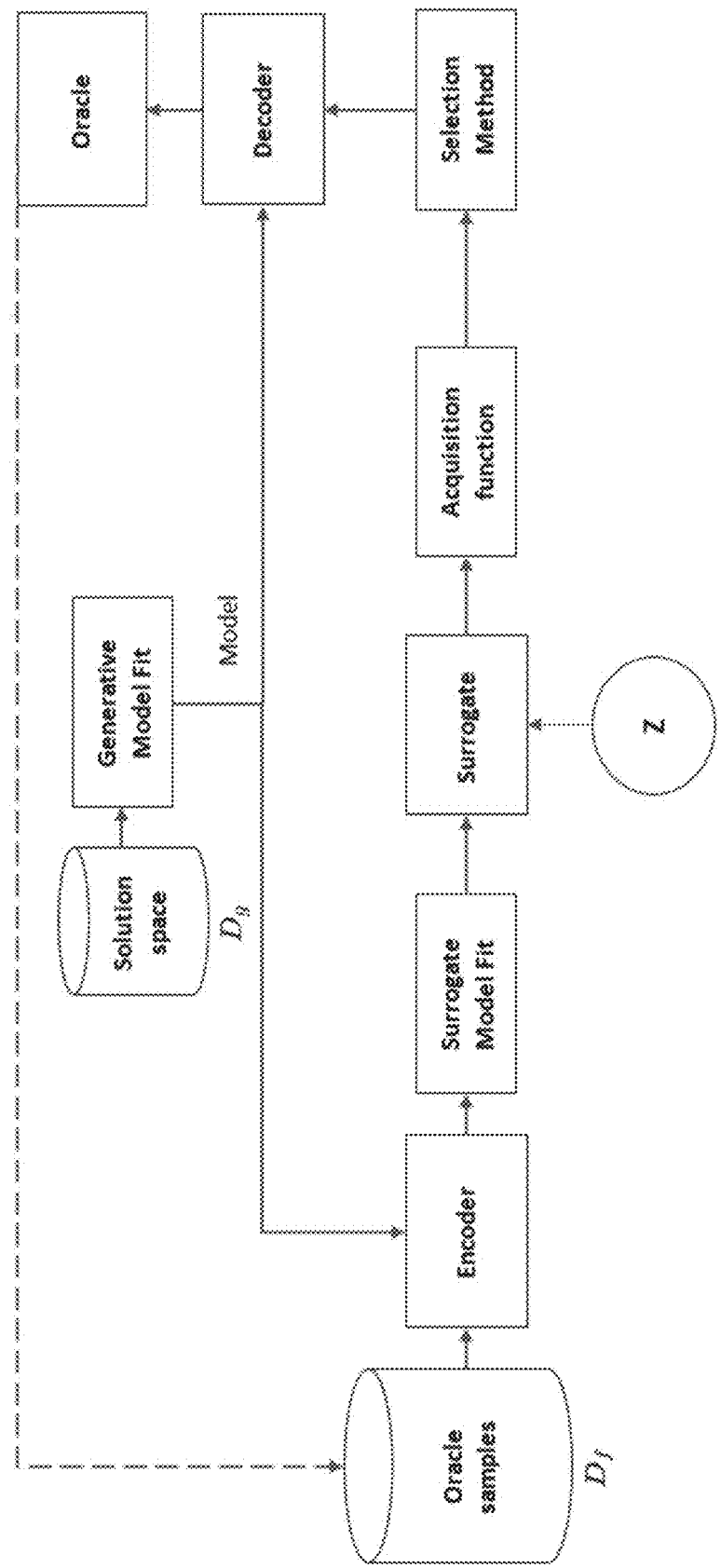
FIG. 17 illustrates the components and process flow of the system for efficiently optimizing a phenotype with a combination of a generative and a predictive model with an encoder/decoder architecture according to an exemplary embodiment.

FIG. 17 illustrates the components and process flow of the system for efficiently optimizing a phenotype with a combination of a generative and a predictive model with an encoder/decoder architecture according to an exemplary embodiment. This figure shows the modifications that can be made to the proposed architecture when the generator is built with an encoder/decoder architecture. Within this formulation, the Encoder module is applied to translate oracle samples into latent space and the surrogate model is trained to use the latent space as input domain. When looking for optimal candidates, the surrogate takes its inputs from a block that samples the latent space $\mathcal{Z}$. The way this space is sampled will depend on the specific architecture of the generator. The Decoder is later applied to all selected samples and maps them to Oracle's domain. Both Encoder and Decoder models are trained by the Generative Model Fit process described earlier.

Guided Generator Training (An Extension of the Generative Process)

The applicant also proposes an extension to the above algorithm. Specifically regarding optimization 1.3. This extension modifies problem 1.3 by including a $\Psi(\bullet)$ and a $\varphi(\bullet)$ function as follows.

$$\theta_G^* = \underset{\theta_G \in \Theta_G}{\operatorname{argmin}} \Psi[\mathbb{P}_G, \mathbb{P}_s, \varphi(\mathbb{P}_G)] \qquad 1.3b$$

Function $\varphi(\bullet)$ represents a measure on the Generator's distribution that quantifies a certain property. And $\Psi(\bullet)$ represents the objective function of the new optimization problem 1.3b. This modification changes the original objective of 1.3 such that it not only optimizes to mimic some real data probability distribution $\mathbb{P}_s$, but also adjusts the generator's parameters $\theta_G$ so that the generator's distribution $\mathbb{P}_G$ has additional features.

This is particularly useful for narrowing down even more the exploration space of the main optimization problem 1.1. For instance, in "Example 1", the solution space $\chi_s$ may still be quite large, due to the number of possible proteins sequence combinations. So a very simple choice for functions $\varphi(\bullet)$ and $\Psi(\bullet)$ that could help with reducing the exploration space, and accelerating the optimization process even more could be the following:

$$\Psi[\mathbb{P}_G, \mathbb{P}_s, \varphi(\mathbb{P}_G)] = D_M[\mathbb{P}_G, \mathbb{P}_s] - \varphi(\mathbb{P}_G)$$

$$\varphi(\mathbb{P}_G) = \mathbb{E}_{x_g \sim \mathbb{P}_g}[E1(x_g)]$$

The first term of the above $\Psi(\bullet)$ objective function ($D_M[\mathbb{P}_G, \mathbb{P}_s]$), will drive the generator's distribution towards the real data probability distribution $\mathbb{P}_s$, while the second term ($\varphi(\mathbb{P}_G)$) will increase the distribution's support on regions of the solution space with a higher Acquisition value. With this particular selection of functions $\Psi(\bullet)$ and $\varphi(\bullet)$, the optimization problem 1.3b might help to achieve a generator with a distribution that accelerates the exploration/exploitation process of the SMBO approach used to solve the main optimization 1.1.

Additional Generation Input (an Extension of the Generative Process)

Besides VAEs, HMMs and other generative models, the proposed method can be implemented considering most GANs approaches. The previous statement includes models that do not rely on a randomized input only, but also ones that use other kinds of input. For example, ACGANs uses a mixed type input which contains a randomized vector as well as label information that is used to condition sample generation. In that case, and in many other approaches where additional information is required, the proposed method can be easily extended. For these situations, the samples used to train the generative model can be described by the expression $D_g = (x_g, w_{gi})_{i=0}^{N_g}$ where $w_{gi} \in W \subseteq \mathbb{R}^{D_w}$ is a vector that contains additional information associated with the sample 'i'. This information may encode not only label descriptors, but also context images, text, etc. Those approaches would require a generative model $G_{\theta_G}: \mathcal{Z}, W \to \chi$ capable of processing that type of information.

Extension to Multi-Objective Optimization

The proposed approach could be extended to multiobjective optimization. Here, instead of optimizing within a scalar target range, these problems are characterized by the existence of an objective function with multidimensional output. This objective function can be described as a set of target functions $f(x) = (f_1(x), f_2(x), \ldots, f_d(x))$ which have to be optimized simultaneously.

There are multiple ways to extend the proposed method to multi-objective optimization. One approach is to apply scalarization of the objective function. This can be achieved by combining all dimensions into one using some other function (e.g., linear combination) and then proceed with the optimization of the scalar result with a single surrogate model. Scalarization can also be achieved by building a model per target component and calculating a score that combines individual predictions. Other approaches are oriented to search for the Pareto front. Within those methods, a model is built for each component and the selection criteria is changed to penalize non-dominant candidates.

Extend the Database with which the Generator is Trained (An Extension of the Generative Process)

In some applications, the Oracle will probably penalize candidates that lie outside the solution space. For example, if the objective is to maximize the production of certain compound within a bacteria by altering some of its genes (where each alteration corresponds to a candidate), the cell may fail to perform the involved metabolic pathway (and won't produce the target compound) if some gene was changed in a way that kills the organism. The gene could be encoding an enzyme that works very well in the isolated pathway, but in the context of the living organism interacts with other elements in a negative way, driving the cell to death. On this type of applications the Oracle will validate solution space compliance as well as the objective function value. This isn't the common scenario in optimization problems, where usually the limits of the solution space are defined by a set of restriction rules and the objective function works in an independent fashion.

In the type of situations where the restrictions of the problem are considered by Oracle's evaluations, the proposed method can be extended to take advantage of that and use Oracle's evaluations not just to train the surrogate model, but also to re-train the generator on each optimization step. This helps to reduce the number of iterations as the generator's knowledge base will grow throughout the process.

Extend Method to Optimize Acquisition by a Newton or Quasi-Newton Method

The main approach considers a Selection Method that optimizes the acquisition function by looking for the best candidates in a set of samples synthesized by the generator. This task can be done in several different ways. The proposed approach can be extended to maximize acquisition by using a newton or quasi-newton method that explores for the best combination of latent space features. Considering this extension, the steps of generating samples and using the selection method to select the top samples can be changed in order to apply a gradient descent algorithm from different starting points and, in that way, obtaining multiple optimal samples.

Figure 18:
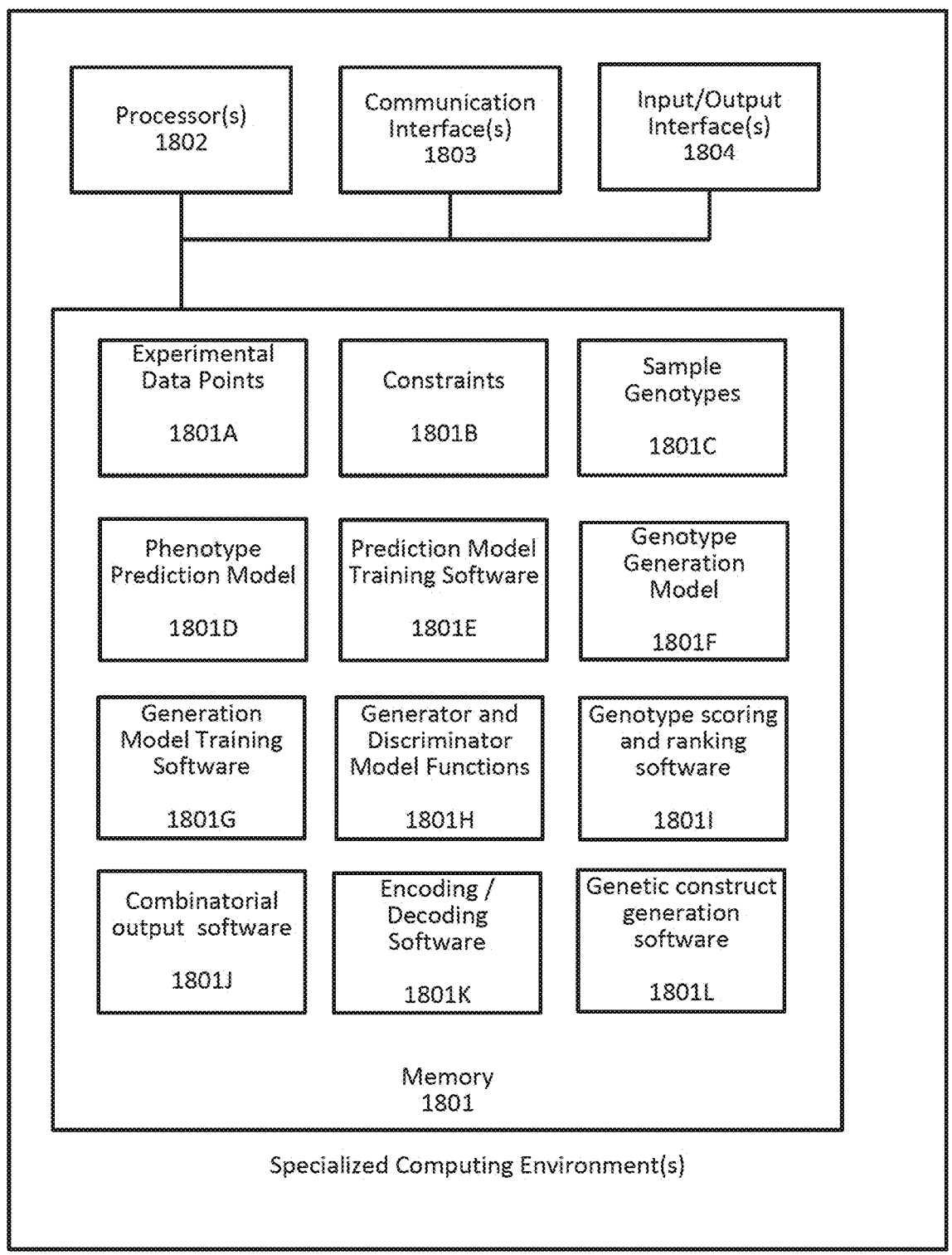
FIG. 18 illustrates the components of a specialized computing environment for efficiently optimizing a phenotype with a combination of a generative and a predictive model according to an exemplary embodiment.

FIG. 18 illustrates the components of a specialized computing environment for efficiently optimizing a phenotype with a combination of a generative and a predictive model according to an exemplary embodiment. Specialized computing environment 1800 can be made up of one or more computing devices that include a memory 1801 that is a non-transitory computer-readable medium and can be volatile memory (e.g., registers, cache, RAM), non-volatile memory (e.g., ROM, EEPROM, flash memory, etc.), or some combination of the two.

As shown in FIG. 18, memory 1801 stores experimental data points 1801A, constraints 1801B, sample genotypes 1801C, phenotype prediction model 1801D, prediction model training software 1801E, genotype generation model 1801F, generation model training software 1801G, generator and discriminator model functions 1801H, genotype scoring and ranking software 18011, combinatorial output software 1801J, encoding/decoding software 1801K, and genetic construct generation software 1801L.

Each of the software components in memory 1801 store specialized instructions and data structures configured to perform the methods for efficiently optimizing a phenotype with a combination of a generative and a predictive model described herein.

All of the software stored within memory 1801 can be stored as a computer-readable instructions, that when executed by one or more processors 1802, cause the processors to perform the functionality described with respect to FIGS. 1-17.

Processor(s) 1802 execute computer-executable instructions and can be a real or virtual processors. In a multi-processing system, multiple processors or multicore processors can be used to execute computer-executable instructions to increase processing power and/or to execute certain software in parallel. As discussed earlier in the application, processors can be processors specialized for the task of training and applying a predictive model, such as graphical processing units (GPUs).

Computing environment 1800 additionally includes a communication interface 1103, such as a network interface, which is used to communicate with devices, applications, or processes on a computer network or computing system, collect data from devices on a network, and implement encryption/decryption actions on network communications within the computer network or on data stored in databases of the computer network. The communication interface conveys information such as computer-executable instructions, audio or video information, or other data in a modulated data signal. A modulated data signal is a signal that has one or more of its characteristics set or changed in such a manner as to encode information in the signal. By way of example, and not limitation, communication media include wired or wireless techniques implemented with an electrical, optical, RF, infrared, acoustic, or other carrier.

Computing environment 1800 further includes input and output interfaces 1304 that allow users (such as system administrators) to provide input to the controller to cause the neurological screening device to display information, to edit data stored in memory 1301, or to perform other administrative functions. For example, an administrator can configure, add, or edit, for example, constraints, encoding software, or experimental data points stored in memory 1801.

An interconnection mechanism (shown as a solid line in FIG. 18), such as a bus, controller, or network interconnects the components of the computing environment 1800.

Input and output interfaces 1804 can be coupled to input and output devices. For example, Universal Serial Bus (USB) ports can allow for the connection of a keyboard, mouse, pen, trackball, touch screen, or game controller, a voice input device, a scanning device, a digital camera, remote control, or another device that provides input to the computing environment.

The computing environment 1800 can additionally utilize a removable or non-removable storage, such as magnetic disks, magnetic tapes or cassettes, CD-ROMs, CD-RWs, DVDs, USB drives, or any other medium which can be used to store information and which can be accessed within the computing environment 1800.

Computing environment 1800 can be a set-top box, personal computer, or one or more servers, for example a farm of networked servers, a clustered server environment, or a cloud network of computing devices.

It will be appreciated by those skilled in the art that changes could be made to the embodiments described above without departing from the broad inventive concept thereof. For example, the steps or order of operation of one of the above-described methods could be rearranged or occur in a different series, as understood by those skilled in the art. It is understood, therefore, that this disclosure is not limited to the particular embodiments disclosed, but it is intended to cover modifications within the spirit and scope of the following claims.

The invention claimed is:

1. A method executed by one or more computing devices for efficiently optimizing a phenotype with a combination of a generative and a predictive model, the method comprising:
    training, by at least one of the one or more computing devices, a phenotype prediction model based at least in part on the plurality of experiential genotype vectors, corresponding phenotype information, and one or more constraints, the phenotype prediction model comprising a surrogate model;
    training, by at least one of the one or more computing devices, a genotype generation model based at least in part on a plurality of sample genotype vectors, the genotype generation model being configured to generate new genotype vectors;
    generating, by at least one of the one or more computing devices, a plurality of new genotype vectors with the genotype generation model;
    applying, by at least one of the one or more computing devices, the phenotype prediction model to the plurality of new genotype vectors to generate a plurality of scores, the phenotype prediction model being configured to predict one or more phenotypic attributes of the new genotype vectors;
    determining, by at least one of the one or more computing devices, a plurality of result genotypes based at least in part on a ranking of the plurality of new genotype vectors according to the plurality of scores; and
    generating, by at least one of the one or more computing devices, a result based at least in part on the plurality of result genotypes, the result indicating one or more genetic constructs for testing.

2. The method of claim 1, further comprising:
receiving, by at least one of the one or more computing devices, one or more constraints, the one or more constraints comprising a plurality of desired phenotypic attributes; and
encoding, by at least one of the one or more computing devices, genotype information corresponding to the one or more constraints in a plurality of experimental data points as the plurality of experiential genotype vectors, the plurality of experimental data points comprising the genotype information and phenotype information corresponding to the genotype information.

3. The method of claim 2, wherein encoding genotype information in a plurality of experimental data points corresponding to the one or more constraints as a plurality of experiential genotype vectors comprises:
identifying the plurality of experimental data points in a database of experimental data points based at least in part on at least one desired phenotypic attribute in the plurality of desired phenotypic attributes; and
encoding genotypes associated with the identified plurality of experimental data points as the plurality of experiential genotype vectors.

4. The method of claim 1, further comprising:
encoding, by at least one of the one or more computing devices, genotype information in a plurality of sample genotypes of a sample database as the plurality of sample genotype vectors.

5. The method of claim 1, wherein the phenotype prediction model is a surrogate model and wherein training a phenotype prediction model based at least in part on the plurality of experiential genotype vectors, the phenotype information, and the one or more constraints comprises:
determining, by at least one of the one or more computing devices, one or more meta-parameters for the phenotype prediction model, the one or more meta-parameters being configured to maximize accuracy of the phenotype prediction model;
determining an objective function based at least in part on the plurality of desired phenotypic attributes; and
iteratively adjusting the objective function by repeatedly selecting one or more experiential genotype vectors in the plurality of experiential genotype vectors that maximize an acquisition function of the phenotype prediction model and updating the objective function based at least in part on one or more experimentally-determined phenotypic attributes corresponding to the one or more experiential genotype vectors.

6. The method of claim 5, wherein applying the phenotype prediction model to the plurality of new genotype vectors to generate a plurality of scores comprises:
applying the objective function to the plurality of new genotype vectors to generate a plurality of prediction scores corresponding to the plurality of new genotype vectors.

7. The method of claim 5, wherein applying the phenotype prediction model to the plurality of new genotype vectors to generate a plurality of scores comprises:
applying an acquisition function of the phenotype prediction model to the plurality of new genotype vectors to generate a plurality of acquisition scores corresponding to the plurality of new genotype vectors.

8. The method of claim 7, wherein generating a result based at least in part on the plurality of result genotypes comprises:
filtering the plurality of result genotype vectors to remove one or more first result genotype vectors corresponding to one or more categories of genotypes having genotype vectors with acquisition scores below acquisition scores of genotype vectors in other categories of genotypes;
selecting a plurality of filtered genotype vectors from the filtered plurality of result genotype vectors, the selected plurality of filtered genotype vectors corresponding to one or more additional categories of genotypes having genotype vectors with acquisition scores above acquisition scores of genotype vectors in other categories of genotypes;
determining a plurality of aggregate acquisition scores corresponding to a plurality of combinations of genotype vectors in the selected plurality of filtered genotype vectors;
ranking the plurality of combinations of genotype vectors according to the plurality of aggregate acquisition scores; and
selecting one or more top-ranked combinations of genotype vectors as the result, wherein each combination of genotype vectors corresponds to two or more genetic constructs for testing.

9. The method of claim 1, wherein training a genotype generation model based at least in part on a plurality of sample genotype vectors, the genotype generation model being configured to generate new genotype vectors comprises:
storing a generator model function having a plurality of trainable generator parameters that is configured to mimic the distribution of the plurality of sample genotype vectors;
storing a discriminator model function having a plurality of trainable discriminator parameters that is configured to estimate a probability that a data sample comes from the plurality of sample genotype vectors instead of from the generator model function;
store a minimax objective function that is configured to be minimized by the generator model function and maximized by the discriminator model function; and
concurrently training both the generator model function and the discriminator model function with the plurality of sample genotype vectors until the minimax objective function converges to a saddle point.

10. The method claim 9, wherein concurrently training both the generator model function and the discriminator model function with the plurality of sample genotype vectors until the minimax objective function converges to a saddle point comprises:
repeatedly sampling one or more sample genotype vectors from the plurality of sample genotype vectors;
repeatedly generating one or more generated genotype vectors with generator model function; and
iteratively applying the discriminator model function to the one or more sample genotype vectors and the one or more generated genotype vectors until the discriminator model function cannot distinguish between the one or more sample genotype vectors and the one or more generated genotype vectors, wherein application of the discriminator model function alternates between the one or more sample genotype vectors and the one or more generated genotype vectors.

11. The method of claim 9, wherein generating a plurality of new genotype vectors with the genotype generation model comprises:
storing one or more parameters, the one or more parameters comprising a batch size and a selection rate; and generating a set of new genotype vectors with the generator model function, the size of the set of new genotype vectors being determined based at least in part on the batch size and the selection rate.

12. The method of claim 1, further comprising:
determining phenotype information corresponding to the one or more result genotype vectors in the plurality of result genotype vectors; and
re-training, by at least one of the one or more computing device, the phenotype prediction model based at least in part on the one or more result genotype vectors, the corresponding phenotype information, and the one or more constraints.

13. A apparatus executed by one or more computing devices for efficiently optimizing a phenotype with a combination of a generative and a predictive model, the apparatus comprising:
one or more processors; and
one or more memories operatively coupled to at least one of the one or more processors and having instructions stored thereon that, when executed by at least one of the one or more processors, cause at least one of the one or more processors to:
train a phenotype prediction model based at least in part on the plurality of experiential genotype vectors, corresponding phenotype information, and one or more constraints, the phenotype prediction model comprising a surrogate model;
train a genotype generation model based at least in part on a plurality of sample genotype vectors, the genotype generation model being configured to generate new genotype vectors;
generate a plurality of new genotype vectors with the genotype generation model;
apply the phenotype prediction model to the plurality of new genotype vectors to generate a plurality of scores, the phenotype prediction model being configured to predict one or more phenotypic attributes of the new genotype vectors;
determine a plurality of result genotypes based at least in part on a ranking of the plurality of new genotype vectors according to the plurality of scores; and
generate a result based at least in part on the plurality of result genotypes, the result indicating one or more genetic constructs for testing.

14. The apparatus of claim 13, wherein at least one of the one or more memories has further instructions stored thereon that, when executed by at least one of the one or more processors, cause at least one of the one or more processors to:
receive one or more constraints, the one or more constraints comprising a plurality of desired phenotypic attributes; and
encode genotype information corresponding to the one or more constraints in a plurality of experimental data points as the plurality of experiential genotype vectors, the plurality of experimental data points comprising the genotype information and phenotype information corresponding to the genotype information.

15. The apparatus of claim 14, wherein the instructions that, when executed by at least one of the one or more processors, cause at least one of the one or more processors to encode genotype information in a plurality of experimental data points corresponding to the one or more constraints as a plurality of experiential genotype vectors further cause at least one of the one or more processors to:
identify the plurality of experimental data points in a database of experimental data points based at least in part on at least one desired phenotypic attribute in the plurality of desired phenotypic attributes; and
encode genotypes associated with the identified plurality of experimental data points as the plurality of experiential genotype vectors.

16. The apparatus of claim 13, wherein at least one of the one or more memories has further instructions stored thereon that, when executed by at least one of the one or more processors, cause at least one of the one or more processors to:
encode genotype information in a plurality of sample genotypes of a sample database as the plurality of sample genotype vectors.

17. The apparatus of claim 13, wherein the phenotype prediction model is a surrogate model and wherein the instructions that, when executed by at least one of the one or more processors, cause at least one of the one or more processors to train a phenotype prediction model based at least in part on the plurality of experiential genotype vectors, the phenotype information, and the one or more constraints further cause at least one of the one or more processors to:
determine one or more meta-parameters for the phenotype prediction model, the one or more meta-parameters being configured to maximize accuracy of the phenotype prediction model;
determine an objective function based at least in part on the plurality of desired phenotypic attributes; and
iteratively adjust the objective function by repeatedly selecting one or more experiential genotype vectors in the plurality of experiential genotype vectors that maximize an acquisition function of the phenotype prediction model and updating the objective function based at least in part on one or more experimentally-determined phenotypic attributes corresponding to the one or more experiential genotype vectors.

18. The apparatus of claim 17, wherein the instructions that, when executed by at least one of the one or more processors, cause at least one of the one or more processors to apply the phenotype prediction model to the plurality of new genotype vectors to generate a plurality of scores further cause at least one of the one or more processors to:
apply the objective function to the plurality of new genotype vectors to generate a plurality of prediction scores corresponding to the plurality of new genotype vectors.

19. The apparatus of claim 17, wherein the instructions that, when executed by at least one of the one or more processors, cause at least one of the one or more processors to apply the phenotype prediction model to the plurality of new genotype vectors to generate a plurality of scores further cause at least one of the one or more processors to:
apply an acquisition function of the phenotype prediction model to the plurality of new genotype vectors to generate a plurality of acquisition scores corresponding to the plurality of new genotype vectors.

20. The apparatus of claim 19, wherein the instructions that, when executed by at least one of the one or more processors, cause at least one of the one or more processors to generate a result based at least in part on the plurality of result genotypes further cause at least one of the one or more processors to:
filter the plurality of result genotype vectors to remove one or more first result genotype vectors corresponding to one or more categories of genotypes having genotype vectors with acquisition scores below acquisition scores of genotype vectors in other categories of genotypes;

select a plurality of filtered genotype vectors from the filtered plurality of result genotype vectors, the selected plurality of filtered genotype vectors corresponding to one or more additional categories of genotypes having genotype vectors with acquisition scores above acquisition scores of genotype vectors in other categories of genotypes;

determine a plurality of aggregate acquisition scores corresponding to a plurality of combinations of genotype vectors in the selected plurality of filtered genotype vectors;

rank the plurality of combinations of genotype vectors according to the plurality of aggregate acquisition scores; and select one or more top-ranked combinations of genotype vectors as the result, wherein each combination of genotype vectors corresponds to two or more genetic constructs for testing.

21. The apparatus of claim 13, wherein the instructions that, when executed by at least one of the one or more processors, cause at least one of the one or more processors to train a genotype generation model based at least in part on a plurality of sample genotype vectors, the genotype generation model being configured to generate new genotype vectors further cause at least one of the one or more processors to:

store a generator model function having a plurality of trainable generator parameters that is configured to mimic the distribution of the plurality of sample genotype vectors;

store a discriminator model function having a plurality of trainable discriminator parameters that is configured to estimate a probability that a data sample comes from the plurality of sample genotype vectors instead of from the generator model function;

store a minimax objective function that is configured to be minimized by the generator model function and maximized by the discriminator model function; and concurrently train both the generator model function and the discriminator model function with the plurality of sample genotype vectors until the minimax objective function converges to a saddle point.

22. The apparatus claim 21, wherein the instructions that, when executed by at least one of the one or more processors, cause at least one of the one or more processors to concurrently train both the generator model function and the discriminator model function with the plurality of sample genotype vectors until the minimax objective function converges to a saddle point further cause at least one of the one or more processors to:

repeatedly sample one or more sample genotype vectors from the plurality of sample genotype vectors;

repeatedly generate one or more generated genotype vectors with generator model function; and iteratively apply the discriminator model function to the one or more sample genotype vectors and the one or more generated genotype vectors until the discriminator model function cannot distinguish between the one or more sample genotype vectors and the one or more generated genotype vectors, wherein application of the discriminator model function alternates between the one or more sample genotype vectors and the one or more generated genotype vectors.

23. The apparatus of claim 21, wherein the instructions that, when executed by at least one of the one or more processors, cause at least one of the one or more processors to generate a plurality of new genotype vectors with the genotype generation model further cause at least one of the one or more processors to:

store one or more parameters, the one or more parameters comprising a batch size and a selection rate; and generate a set of new genotype vectors with the generator model function, the size of the set of new genotype vectors being determined based at least in part on the batch size and the selection rate.

24. The apparatus of claim 13, wherein at least one of the one or more memories has further instructions stored thereon that, when executed by at least one of the one or more processors, cause at least one of the one or more processors to:

determine phenotype information corresponding to the one or more result genotype vectors in the plurality of result genotype vectors; and re-train the phenotype prediction model based at least in part on the one or more result genotype vectors, the corresponding phenotype information, and the one or more constraints.

25. At least one non-transitory computer-readable medium storing computer-readable instructions for efficiently optimizing a phenotype with a combination of a generative and a predictive model that, when executed by one or more computing devices, cause at least one of the one or more computing devices to:

train a phenotype prediction model based at least in part on the plurality of experiential genotype vectors, corresponding phenotype information, and one or more constraints, the phenotype prediction model comprising a surrogate model;

train a genotype generation model based at least in part on a plurality of sample genotype vectors, the genotype generation model being configured to generate new genotype vectors;

generate a plurality of new genotype vectors with the genotype generation model;

apply the phenotype prediction model to the plurality of new genotype vectors to generate a plurality of scores, the phenotype prediction model being configured to predict one or more phenotypic attributes of the new genotype vectors;

determine a plurality of result genotypes based at least in part on a ranking of the plurality of new genotype vectors according to the plurality of scores; and generate a result based at least in part on the plurality of result genotypes, the result indicating one or more genetic constructs for testing.

26. The at least one non-transitory computer-readable medium of claim 25, further storing computer-readable instructions that, when executed by at least one of the one or more computing devices, cause at least one of the one or more computing devices to:

receive one or more constraints, the one or more constraints comprising a plurality of desired phenotypic attributes; and encode genotype information corresponding to the one or more constraints in a plurality of experimental data points as the plurality of experiential genotype vectors, the plurality of experimental data points comprising the genotype information and phenotype information corresponding to the genotype information.

27. The at least one non-transitory computer-readable medium of claim 26, wherein the instructions that, when executed by at least one of the one or more computing devices, cause at least one of the one or more computing devices to encode genotype information in a plurality of experimental data points corresponding to the one or more constraints as a plurality of experiential genotype vectors further cause at least one of the one or more computing devices to:
  identify the plurality of experimental data points in a database of experimental data points based at least in part on at least one desired phenotypic attribute in the plurality of desired phenotypic attributes; and
  encode genotypes associated with the identified plurality of experimental data points as the plurality of experiential genotype vectors.

28. The at least one non-transitory computer-readable medium of claim 25, further storing computer-readable instructions that, when executed by at least one of the one or more computing devices, cause at least one of the one or more computing devices to:
  encode genotype information in a plurality of sample genotypes of a sample database as the plurality of sample genotype vectors.

29. The at least one non-transitory computer-readable medium of claim 25, wherein the phenotype prediction model is a surrogate model and wherein the instructions that, when executed by at least one of the one or more computing devices, cause at least one of the one or more computing devices to train a phenotype prediction model based at least in part on the plurality of experiential genotype vectors, the phenotype information, and the one or more constraints further cause at least one of the one or more computing devices to:
  determine one or more meta-parameters for the phenotype prediction model, the one or more meta-parameters being configured to maximize accuracy of the phenotype prediction model;
  determine an objective function based at least in part on the plurality of desired phenotypic attributes; and
  iteratively adjust the objective function by repeatedly selecting one or more experiential genotype vectors in the plurality of experiential genotype vectors that maximize an acquisition function of the phenotype prediction model and updating the objective function based at least in part on one or more experimentally-determined phenotypic attributes corresponding to the one or more experiential genotype vectors.

30. The at least one non-transitory computer-readable medium of claim 29, wherein the instructions that, when executed by at least one of the one or more computing devices, cause at least one of the one or more computing devices to apply the phenotype prediction model to the plurality of new genotype vectors to generate a plurality of scores further cause at least one of the one or more computing devices to:
  apply the objective function to the plurality of new genotype vectors to generate a plurality of prediction scores corresponding to the plurality of new genotype vectors.

31. The at least one non-transitory computer-readable medium of claim 29, wherein the instructions that, when executed by at least one of the one or more computing devices, cause at least one of the one or more computing devices to apply the phenotype prediction model to the plurality of new genotype vectors to generate a plurality of scores further cause at least one of the one or more computing devices to:
  apply an acquisition function of the phenotype prediction model to the plurality of new genotype vectors to generate a plurality of acquisition scores corresponding to the plurality of new genotype vectors.

32. The at least one non-transitory computer-readable medium of claim 31, wherein the instructions that, when executed by at least one of the one or more computing devices, cause at least one of the one or more computing devices to generate a result based at least in part on the plurality of result genotypes further cause at least one of the one or more computing devices to:
  filter the plurality of result genotype vectors to remove one or more first result genotype vectors corresponding to one or more categories of genotypes having genotype vectors with acquisition scores below acquisition scores of genotype vectors in other categories of genotypes;
  select a plurality of filtered genotype vectors from the filtered plurality of result genotype vectors, the selected plurality of filtered genotype vectors corresponding to one or more additional categories of genotypes having genotype vectors with acquisition scores above acquisition scores of genotype vectors in other categories of genotypes;
  determine a plurality of aggregate acquisition scores corresponding to a plurality of combinations of genotype vectors in the selected plurality of filtered genotype vectors;
  rank the plurality of combinations of genotype vectors according to the plurality of aggregate acquisition scores; and
  select one or more top-ranked combinations of genotype vectors as the result, wherein each combination of genotype vectors corresponds to two or more genetic constructs for testing.

33. The at least one non-transitory computer-readable medium of claim 25, wherein the instructions that, when executed by at least one of the one or more computing devices, cause at least one of the one or more computing devices to train a genotype generation model based at least in part on a plurality of sample genotype vectors, the genotype generation model being configured to generate new genotype vectors further cause at least one of the one or more computing devices to:
  store a generator model function having a plurality of trainable generator parameters that is configured to mimic the distribution of the plurality of sample genotype vectors;
  store a discriminator model function having a plurality of trainable discriminator parameters that is configured to estimate a probability that a data sample comes from the plurality of sample genotype vectors instead of from the generator model function;
  store a minimax objective function that is configured to be minimized by the generator model function and maximized by the discriminator model function; and
  concurrently train both the generator model function and the discriminator model function with the plurality of sample genotype vectors until the minimax objective function converges to a saddle point.

34. The at least one non-transitory computer-readable medium claim 33, wherein the instructions that, when executed by at least one of the one or more computing devices, cause at least one of the one or more computing devices to concurrently train both the generator model function and the discriminator model function with the plurality of sample genotype vectors until the minimax objective function converges to a saddle point further cause at least one of the one or more computing devices to:

repeatedly sample one or more sample genotype vectors from the plurality of sample genotype vectors;

repeatedly generate one or more generated genotype vectors with generator model function; and iteratively apply the discriminator model function to the one or more sample genotype vectors and the one or more generated genotype vectors until the discriminator model function cannot distinguish between the one or more sample genotype vectors and the one or more generated genotype vectors, wherein application of the discriminator model function alternates between the one or more sample genotype vectors and the one or more generated genotype vectors.

35. The at least one non-transitory computer-readable medium of claim 33, wherein the instructions that, when executed by at least one of the one or more computing devices, cause at least one of the one or more computing devices to generate a plurality of new genotype vectors with the genotype generation model further cause at least one of the one or more computing devices to:

store one or more parameters, the one or more parameters comprising a batch size and a selection rate; and generate a set of new genotype vectors with the generator model function, the size of the set of new genotype vectors being determined based at least in part on the batch size and the selection rate.

36. The at least one non-transitory computer-readable medium of claim 25, further storing computer-readable instructions that, when executed by at least one of the one or more computing devices, cause at least one of the one or more computing devices to:

determine phenotype information corresponding to the one or more result genotype vectors in the plurality of result genotype vectors; and re-train the phenotype prediction model based at least in part on the one or more result genotype vectors, the corresponding phenotype information, and the one or more constraints.

* * * * *